(12) United States Patent
Alonso et al.

(10) Patent No.: US 8,501,817 B2
(45) Date of Patent: Aug. 6, 2013

(54) STABILIZED COMPOSITIONS OF ALKYLATING AGENTS AND METHODS OF USING SAME

(75) Inventors: Robert Alonso, Rye, NH (US); Barry R. Walker, Bryn Mawr, PA (US); Peter A. Crooks, Nicholasville, KY (US)

(73) Assignee: Ceptaris Therapeutics, Inc., Malvern, PA (US)

( * ) Notice: Subject to any disclaimer, the term of this patent is extended or adjusted under 35 U.S.C. 154(b) by 634 days.

(21) Appl. No.: 12/401,812

(22) Filed: Mar. 11, 2009

(65) Prior Publication Data

US 2010/0029783 A9    Feb. 4, 2010

Related U.S. Application Data

(63) Continuation-in-part of application No. 11/369,305, filed on Mar. 7, 2006.

(60) Provisional application No. 61/039,840, filed on Mar. 27, 2008, provisional application No. 60/661,356, filed on Mar. 14, 2005, provisional application No. 60/751,128, filed on Dec. 16, 2005.

(51) Int. Cl.
*A01N 33/02*     (2006.01)
*A61K 31/13*     (2006.01)
*C07C 211/00*    (2006.01)

(52) U.S. Cl.
USPC ............................ 514/672; 424/400; 564/463

(58) Field of Classification Search
USPC ............................ 514/672; 424/400; 564/463
See application file for complete search history.

(56) References Cited

U.S. PATENT DOCUMENTS

| | | |
|---|---|---|
| 3,767,792 A | 10/1973 | Cook et al. |
| 3,904,766 A | 9/1975 | Van Scott et al. |
| 4,083,692 A | 4/1978 | Epstein et al. |
| 4,206,222 A | 6/1980 | Valetas |
| 4,725,438 A | 2/1988 | Leazer |
| 4,853,388 A | 8/1989 | Pearlman |
| 4,863,910 A | 9/1989 | Takayanagi |
| 4,888,344 A | 12/1989 | Sunagawa et al. |
| 4,888,354 A | 12/1989 | Chang et al. |
| 4,949,641 A | 8/1990 | Sayles |
| 5,051,363 A | 9/1991 | Ritter et al. |
| 5,229,422 A | 7/1993 | Takahashi et al. |
| 5,326,790 A | 7/1994 | Thornfeldt |
| 5,616,332 A | 4/1997 | Herstein |
| 5,719,197 A | 2/1998 | Kanios et al. |
| 5,744,460 A * | 4/1998 | Muller et al. ............... 514/44 A |
| 5,820,872 A | 10/1998 | Edelson et al. |
| 5,824,650 A | 10/1998 | De Lacharriere et al. |
| 5,948,437 A | 9/1999 | Parikh et al. |
| 5,972,892 A | 10/1999 | De Lacharriere et al. |
| 6,005,002 A | 12/1999 | Springer et al. |
| 6,017,902 A | 1/2000 | Glass et al. |
| 6,124,108 A | 9/2000 | Prabhati |
| 6,255,502 B1 | 7/2001 | Penkler et al. |
| 6,329,148 B1 | 12/2001 | Rosen et al. |
| 6,472,435 B1 | 10/2002 | Boyle |
| 6,692,742 B1 | 2/2004 | Nakamura et al. |
| 6,753,155 B1 | 6/2004 | Prabhati |
| 7,323,171 B2 | 1/2008 | Wallner et al. |
| 7,470,433 B2 * | 12/2008 | Carrara et al. ............... 424/448 |
| 2001/0049349 A1 | 12/2001 | Chinery et al. |
| 2002/0142028 A1 | 10/2002 | Elliesen et al. |
| 2002/0146692 A1 | 10/2002 | Yamazaki et al. |
| 2003/0083321 A1 | 5/2003 | Lerner et al. |
| 2003/0087961 A1 | 5/2003 | Ko et al. |
| 2003/0215471 A1 * | 11/2003 | Wilmott et al. ............... 424/401 |
| 2005/0039228 A1 | 2/2005 | Ding et al. |
| 2006/0079492 A1 * | 4/2006 | Ahlem et al. ............... 514/178 |
| 2006/0205694 A1 | 9/2006 | Alonso et al. |
| 2006/0281720 A1 | 12/2006 | Loria |
| 2007/0287719 A1 | 12/2007 | Boyden et al. |
| 2008/0194699 A1 | 8/2008 | Alonso et al. |
| 2009/0312290 A1 * | 12/2009 | Panasci et al. ............... 514/110 |
| 2010/0029783 A9 | 2/2010 | Alonso et al. |
| 2010/0041767 A1 | 2/2010 | Alonso et al. |
| 2011/0039943 A1 | 2/2011 | Alonso et al. |
| 2011/0065803 A1 | 3/2011 | Alonso et al. |

FOREIGN PATENT DOCUMENTS

| | | |
|---|---|---|
| EP | 0317281 | 7/1987 |
| WO | WO 87/04154 | 7/1987 |
| WO | WO 9942578 A2 * | 8/1999 |
| WO | WO03037380 A1 | 8/2003 |

(Continued)

OTHER PUBLICATIONS

Morissette et al. "High-throughput crystallization: polymorphs, salts, co-crystals and solvates of pharmaceutical solids" Advanced Drug Delivery Reviews, 2004, vol. 56, pp. 275-300.*
PubMed (http://pubchem.ncbi.nlm.nih.gov/summary/summary.cgi?cid=121547, obtained Aug. 8, 2012).*
Bonina et al., Vehicle effects on in vitro skin permeation of and stratum corneum affinity for model drugs caffeine and testosterone, Int J Pharmaceutics, 100:41-47, 1993.
Khan et al., "Hepatocyte toxicity of mechlorethamine and other alkylating anticancer drugs. Role of lipid peroxidation," Biochem Pharmacol 43(9):1963-7 (1992).
Kravitz et al., Topical nitrogen mustard induced carcinogenesis, Acta Derm Venereol, 1978 (abstract).
Lessin et al., Testing efficacy and safety of topical nitrogen mustard in mycosis fungoides, submitted to 21$^{st}$ World Congress of Dermatology in Buenos Aires, Oct. 1-5, 2007.
Lessin, Nitrogen mustard (NM) ointment formulation containing propylene glycol (PG) is active in treating mycosis fungoides (MF), J Inv Dermatol, 2007 (abstract).

(Continued)

*Primary Examiner* — Kendra D Carter
(74) *Attorney, Agent, or Firm* — Wilson Sonsini Goodrich & Rosati

(57) ABSTRACT

A composition and method for treatment of cancer. The composition for treating a skin disorder, comprising: an alkylating agent such as, for example, a Nitrogen Mustard or an HX salt of the Nitrogen Mustard, wherein the alkylating agent is in a non-aqueous vehicle or carrier that does not include petrolatum or ethanol does not include petrolatum or ethanol. The method comprises topically applying the composition of the alkylating agent to the affected skin, wherein the alkylating agent is in a non-aqueous vehicle or carrier that does not include petrolatum or ethanol.

11 Claims, 5 Drawing Sheets

FOREIGN PATENT DOCUMENTS

| | | |
|---|---|---|
| WO | WO 2004050057 A2 | 6/2004 |
| WO | WO 2005/007129 A2 | 1/2005 |
| WO | WO 2005/007129 A3 | 8/2005 |
| WO | WO 2006/099385 | 9/2006 |
| WO | WO 2009/120493 | 10/2009 |

OTHER PUBLICATIONS

Ritschel, et al., Stability of the nitrogen mustard mechlorethamine in novel formulations for dermatological use, Int'l J. Pharm., 362: 67-73, 2008.

Wormser et al., Noninvasive procedure for in situ determination of skin surface aspartic proteinase activity in animals; implications for human skin, Arch Dermatol Res, 289: 686-691, 1997.

Wu et al., "Elucidation of the chemical structures of natural antioxidants isolated from rosemary," JAOCS 59(8):339-345 (1982).

Non-final office action mailed Dec. 24, 2009 in U.S. Appl. No. 11/369,305, currently under examination at the USPTO.

Non-final office action mailed Feb. 19, 2010 in U.S. Appl. No. 11/908,531, currently under examination at the USPTO.

PCT/US2006/009060 International Search Report mailed Jan. 28, 2008.

PCT/US2009/036737 International Search Report mailed Jan. 11, 2010.

Alonso et al., U.S. Appl. No. 12/687,605, filed Jan. 14, 2010, entitled "Stabilized compositions of alkylating agents and methods of using same," currently pending.

European search report and opinion dated Mar. 31, 2008 for EP Application No. 06738150.9.

Cummings, J., et al., "The Long Term Stability of Mechlorethamine Hydrochloride (Nitrogen Mustard) Ointment Measured by HPLC", J. Pharm. Pharmacol. 45: 6-9 1993.

Price, Norman M., "Ointment-Based Mechlorethamine Treatment for Mycosis Fungoides", Cancer, 52, 2214-2219 (1983).

Kim, Youn, H., "Topical Nitrogen Mustard in the Management of Mycosis Fungoides, Update of the Stanford Experience", ARCH Dermatol., 139, 165-173 (Feb. 2003).

Arrazola et al., "Treatment of alopecia areata with topical nitrogen mustard," Int J Dermatol 24(9):608-10, 1985.

Bernardo et al., "Topical nitrogen mustard in the treatment of alopecia areata: a bilateral comparison study," J Am Acad Dermatol 49(2):291-4, 2003.

Connors et al., "Mechlorethamine," Chemical Stability of Pharmaceuticals. A Handbook for Pharmacists, Second Edition (John Wiley & Sons, Inc.) pp. 529-533, 1986.

Tang et al., "Topical mechlorethamine restores autoimmune-arrested follicular activity in mice with an alopecia areata-like disease by targeting infiltrated lymphocytes," J Invest Dermatol 120(3):400-6, 2003.

Final office action mailed on Jul. 6, 2010 in connection with U.S. Appl. No. 11/908,531.

Non-final office action mailed on Jan. 27, 2011 in connection with U.S. Appl. No. 11/908,531.

Taylor, R.J: Halprin, K.M.: Levine, V.; Aoyagi, T. Mechlorethamine Hydrochloride Solutions and Ointment Prolonged Stability and Biological Activity, Archives of Dermatology, Jul. 1980, vol. 116(7), pp. 783-785.

Liren Tang et al., "Topical Mechlorethamine Restores Autoimmune-Arrested Follicular Activity in Mice with an Alopecia Areata-Like Disease by Targeting Infiltrated Lymphocytes", J. Investigative Derm., 120(3) 400-406 (2003).

P. Foulec et al., "Evaluation of a 1-h exposure time to mechlorethamine in patients undergoing topical treatment", Brit. J. Derm. 147, 926-930 (2002).

Youn H. Kim, MD; Gina Martinez, BA; Anna Varghese, BA; Richard T. Hoppe, MD, Topical Nitrogen Mustard in the Management of Mycosis Fungoides, Arch Dermatol. 2003;139:165-173.

Mechlorethamine (Topical), Drugs.com Drug information online www.drugs.com/mmx/mechlorethamine-hydrochloride.html, Jun. 14, 2010.

Chabner et al., "Antineoplastic agents," Goodman & Gilman's The Pharmacological Basis of Therapeutics, Tenth Edition, Chapter 52, pp. 1389-1397, 2001.

Bell, "The effect of the solvent on protolytic equilibria," The Proton in Chemistry, Second Edition (Cornell University Press) pp. 44-55, 1959.

Non-final office action mailed Jun. 10, 2010 in connection with U.S. Appl. No. 12/549,258.

U.S. Appl. No. 13/300,021, filed Nov. 18, 2011, Alonso et al.

Ash, et al. Handbook of preservatives. Synapse Information Resources, Inc. 2004, pp. 292, 294 and 379.

Office action dated Jan. 27, 2011 for U.S. Appl. No. 11/908,531.
Office action dated Feb. 19, 2010 for U.S. Appl. No. 11/908,531.
Office action dated Mar. 8, 2012 for U.S. Appl. No. 11/908,531.
Office action dated May 18, 2012 for U.S. Appl. No. 12/687,605.
Office action dated May 24, 2012 for U.S. Appl. No. 12/948,593.
Office action dated Jul. 6, 2010 for U.S. Appl. No. 11/908,531.
Office action dated Aug. 31, 2011 for U.S. Appl. No. 11/908,531.
Office action dated Nov. 3, 2011 for U.S. Appl. No. 12/687,605.
Office action dated Nov. 9, 2011 for U.S. Appl. No. 12/948,593.

International search report and written opinion dated Sep. 18, 2012 for PCT/US2012/046155.

Notice of allowance dated Oct. 5, 2012 for U.S. Appl. No. 11/908,531.

Notice of allowance dated Jan. 8, 2013 for U.S. Appl. No. 11/908,531.

Notice of allowance dated Oct. 23, 2012 for U.S. Appl. No. 12/687,605.

Office action dated Oct. 9, 2012 for U.S. Appl. No. 12/890,183.

de Quatrebarbes J, et al. Treatment of early-stage mycosis fungoides with twice-weekly applications of mechlorethamine and topical corticosteroids: a prospective study. Arch Dermatol. Sep. 2005;141(9):1117-20.

Reepmeyer, JC. Analysis of the nitrogen mustard mechlorethamine in topical pharmaceutical preparations by high-performance liquid chromatography. J Chromatogr A. Sep. 2, 2005;1085(2):262-9.

* cited by examiner

Log-linear plot of the stability of MCHCl in Transcutol P™ (2-(2-ethoxyethoxy) ethanol) at various temperatures over time.

STABILIZED COMPOSITIONS OF ALKYLATING AGENTS AND METHODS OF USING SAME

The present patent application is a continuation-in-part of U.S. application Ser. No. 11/369,305, filed Mar. 7, 2006, which claims priority from U.S. provisional application Ser. Nos. 60/751,128, filed Dec. 16, 2005, and 60/661,356, filed Mar. 14, 2005. The present patent application is also a non-provisional application claiming priority from provisional application with Ser. No. 61/039,840 (filed Mar. 27, 2008 and titled "Stabilized Compositions of Alkylating Agents and Methods of Using Same").

FIELD OF THE INVENTION

The present invention relates generally to compositions of alkylating agents and method using the compositions for topical treatment of skin disease, and more specifically to a stabilized Nitrogen Mustard composition and method of use for topically treating the skin disease.

BACKGROUND

Alkylating agents may be used in the pharmaceutical industry as anticancer drugs. Therefore, there is a need for improved alkylating agents.

SUMMARY OF THE INVENTION

A first aspect of the present invention provides a dispersion, comprising: between about 0.001% and about 2.0% by weight of an alkylating agent, or pharmaceutically acceptable salts, polymorphs, or solvates thereof; and between about 15% and about 60% by weight of a pharmaceutically acceptable excipient. The pharmaceutically acceptable excipient may be 2-(2-ethoxyethoxy) ethanol. The alkylating agent may be MCHCl.

A second aspect of the present invention provides a method for treating a person with a skin disorder, comprising: topically applying a dispersion to the affected skin, wherein the dispersion comprises between about 0.001% and about 2.0% by weight of an alkylating agent, or pharmaceutically acceptable salts, polymorphs or solvates thereof; and between about 15% and about 60% by weight of a pharmaceutically acceptable excipient. The pharmaceutically acceptable excipient may be 2-(2-ethoxyethoxy) ethanol. The alkylating agent may be MCHCl.

A third aspect of the present invention provides a method for stabilizing a volatile alkylating agent, comprising: dispersing between about 0.001% and about 2.0% by weight of an alkylating agent, or pharmaceutically acceptable salts, polymorphs or solvates thereof and between about 15% and about 60% by weight of a pharmaceutically acceptable excipient. The pharmaceutically acceptable excipient may be 2-(2-ethoxyethoxy) ethanol. The alkylating agent may be MCHCl.

A fourth aspect of the present invention provides a method for stabilizing a nitrogen mustard or pharmaceutically acceptable HX salt of the nitrogen mustard, comprising dispersing the nitrogen mustard or pharmaceutically acceptable HX salt of the nitrogen mustard in between about 0.001% and about 2.0% by weight of an alkylating agent, or pharmaceutically acceptable salts, polymorphs, or solvates thereof and between about 15% and about 60% by weight of a pharmaceutically acceptable excipient. The pharmaceutically acceptable excipient may be 2-(2-ethoxyethoxy) ethanol. The alkylating agent may be MCHCl.

A fifth aspect of the present invention provides a method of treating vitiligo, comprising administering a dispersion to a person in need thereof, wherein the dispersion comprises between about 0.001% and about 2.0% by weight of an alkylating agent, or pharmaceutically acceptable salts, polymorphs, or solvates thereof and between about 15% and about 60% by weight of a pharmaceutically acceptable excipient. The pharmaceutically acceptable excipient may be 2-(2-ethoxyethoxy) ethanol. The alkylating agent may be MCHCl.

A sixth aspect of the present invention provides a method of formulating a pharmaceutical product, a component of which is an at least one hydrolytically unstable alkylating agent(s), comprising: providing a formulation aid, wherein said formulation aid is a pre-solvated or pre-dispersed form of the alkylating agent; and dispersing the formulation aid into a pharmaceutical formulation or other preparation, wherein the formulation aid and the pharmaceutical formulation are substantially homogeneous.

A seventh aspect of the present invention provides a provides a composition for treating a skin disorder, comprising: a Nitrogen Mustard or an HX salt of the Nitrogen Mustard, wherein the Nitrogen Mustard or the HX salt of the Nitrogen Mustard is in a non-aqueous vehicle or carrier, wherein the non-aqueous vehicle or carrier comprises between about 15% and about 60% by weight of a pharmaceutically acceptable excipient, wherein the Nitrogen Mustard is represented by the following structures:

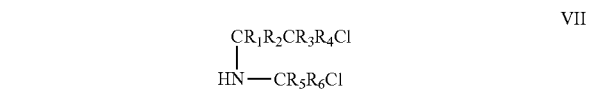

VII

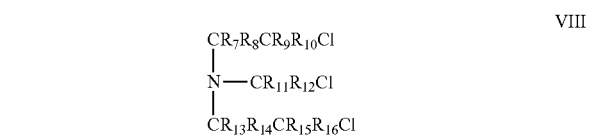

VIII

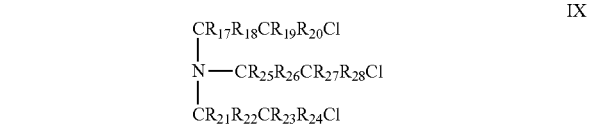

IX

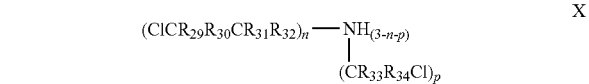

X wherein each $R_1, R_2, R_3 \ldots R_{34}$ ($R_1$-$R_{34}$) is independently selected from the group consisting of H, linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, aryl groups, aralkyl groups, alkaryl groups, cycloalkyl groups, bicycloalkyl groups, alkenyl groups, alkalkenyl groups, and alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups alkylenylacyl groups and alkynylacyl groups, wherein n is 1, 2, . . . 3, wherein p is 0, 1, . . . 2, wherein n+p≦3, and wherein any two $R_1$-$R_{34}$ in the same molecule may be linked to form a three- to eight-membered cyclic group. The pharmaceutically acceptable excipient may be 2-(2-ethoxyethoxy) ethanol. The alkylating agent may be MCHCl.

An eighth aspect of the present invention provides a method for treating a skin disorder, comprising: administering to a person in need thereof a composition, comprising: a Nitrogen Mustard or an HX salt of the Nitrogen Mustard, wherein the Nitrogen Mustard or the HX salt of the Nitrogen Mustard is in a non-aqueous vehicle or carrier, wherein the non-aqueous vehicle or carrier comprises between about 15% and about 60% by weight of a pharmaceutically acceptable excipient, wherein the Nitrogen Mustard is represented by the following structures:

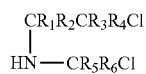

VII

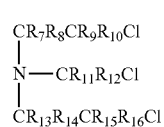

VIII

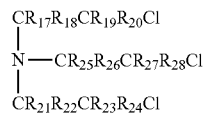

IX

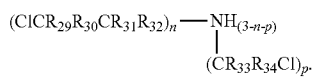

X wherein each $R_1$, $R_2$, $R_3$ . . . $R_{34}$ ($R_1$-$R_{34}$) is independently selected from the group consisting of H, linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, aryl groups, aralkyl groups, alkaryl groups, cycloalkyl groups, bicycloalkyl groups, alkenyl groups, alkalkenyl groups, and alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups alkylenylacyl groups and alkynylacyl groups, wherein n is 1, 2, . . . 3, wherein p is 0, 1, . . . 2, wherein n+p≦3, and wherein any two $R_1$-$R_{34}$ in the same molecule may be linked to form a three- to eight-membered cyclic group. The pharmaceutically acceptable excipient may be 2-(2-ethoxyethoxy) ethanol. The alkylating agent may be MCHCl.

BRIEF DESCRIPTION OF THE DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION OF THE INVENTION

Figure 1:
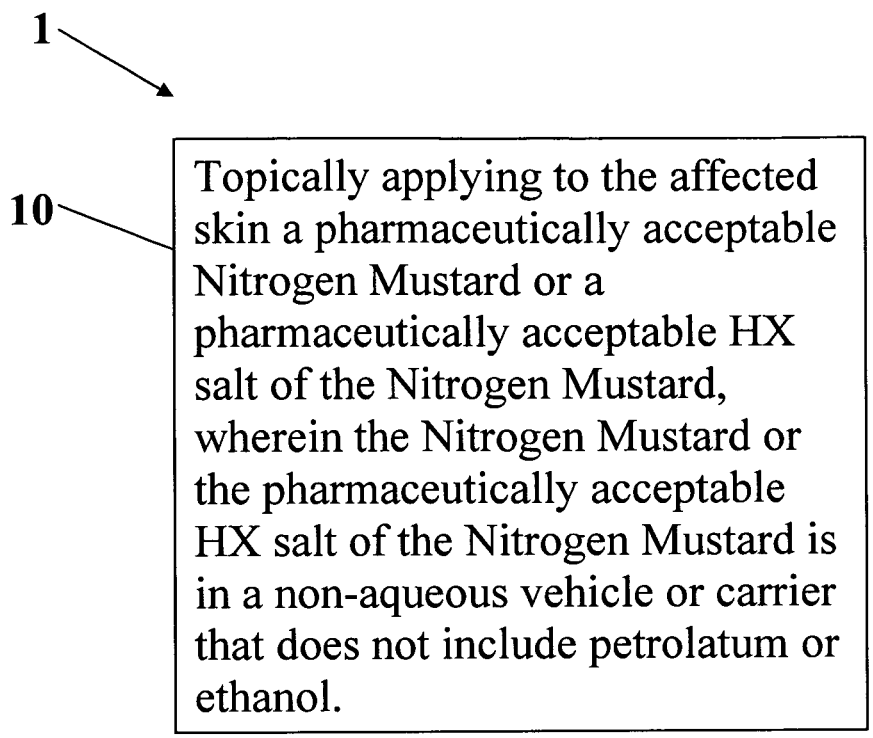
FIG. 1 illustrates a method for the use of compositions having stabilized alkylating agents for treating skin disease, in accordance with embodiments of the present invention.

Alkylating agents, such as nitrogen mustard (Mechlorethamine) may be used in the pharmaceutical industry as anti-cancer drugs. For example, in theory, the aziridinium cation, (Structure II), may undergo nucleophilic attack by an electron donor,

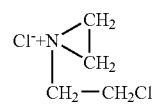

II resulting in alkylating the nucleophile. For example, reaction with the nucleophile guanine (G), structure III, shown in Reaction 2, at position N-7 of the guanine (G) occurs to the greatest extent. Other sites on guanine (G), and other DNA bases such as adenine (A), cytosine (C) and thymine (T), and phosphate oxygens also can be alkylated.

Reaction 2: Nucleophilic attack by guanine on the unstable aziridinium ring.

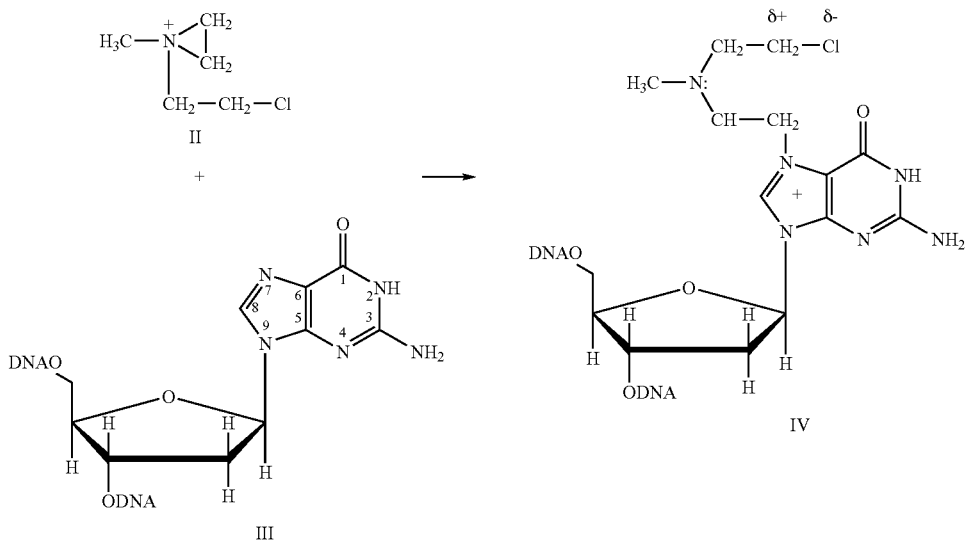

Unfortunately, the electrophilicity of alkylating agents, such as nitrogen mustards, causes them to be subject to decomposition in the presence of natural nucleophiles in the environment, such as water. There is a need for stabilizing alkylating agents to protect them from nucleophilic attack by nucleophiles in the environment.

Cutaneous T-cell lymphoma (CTCL) is a malignancy of the T-helper (CD4+) cells of the immune system. CTCL, also known as mycosis fungoides (MF), is a cancer of the white blood cells that primarily affects the skin and only secondarily affects other sites. This disease involves the uncontrolled proliferation of T-lymphocytes known as T-helper cells, so named because of their role in the immune response. T-helper cells are characterized by the presence of a protein receptor on their surface called CD4. Accordingly, T-helper cells are said to be CD4+.

The proliferation of T-helper cells results in the penetration, or infiltration, of these abnormal cells into the epidermal layer of the skin. The skin reacts with slightly scaling lesions that itch, although the sites of greatest infiltration do not necessarily correspond to the sites of the lesions. The lesions are most often located on the trunk, but can be present on any part of the body. In the most common course of the disease, the patchy lesions progress to palpable plaques that are deeper red and have more defined edges. As the disease worsens, skin tumors develop that are often mushroom-shaped, hence the name mycosis fungoides. Finally, the cancer progresses to extracutanous involvement, often in the lymph nodes or the viscera.

CTCL is a rare disease, with an annual incidence of about 0.29 cases per 100,000 persons in the United States. It is about half as common in Eastern Europe. However, this discrepancy may be attributed to a differing physician awareness of the disease rather than a true difference in occurrence. In the Unites States, there are about 500-600 new cases a year and about 100-200 deaths. CTCL is usually seen in older adults; the median age at diagnosis is 55-60 years. It strikes twice as many men as women. The average life expectancy at diagnosis is 7-10 years, even without treatment.

The most common side effect for treatments applied to the skin is skin hypersensitivity to the drug. There is a need for improved compositions and methods for skin diseases that avoid or minimize skin hypersensitivity to the drug.

In an embodiment, patients having MF topically treated with Nitrogen Mustard compounded into a polypropylene glycol (PPG, molecular weight from about 300 to about 2500), propylene glycol (PG,), polyethyleneglycol (PEG, molecular weight from about 100 to about 1000) or ethylene glycol ointment or cream showed no evidence of any systemic toxicities.

Table 1 below provides a summary of topical treatment of patients having MF with nitrogen mustard in propylene glycol (PG), including response rates and toxicities.

TABLE 1

Topical Nitrogen Mustard In Mycosis Fungoides (MF): Summary Of Clinical Outcomes & Toxicities.

| #PTS | F/U (YRS) | VEHICLE | DOSE | % CR | % PCR | % HYPER-SENSITIVITY REACTIONS | % SYSTEMIC TOXICITIES* |
|---|---|---|---|---|---|---|---|
| 14 | <1 | PG | 10 mg % Topically Applied Once Daily | 36% | 42% | 7% | 0% |

*Systemic toxicities monitored by serial History & Physicals and laboratory studies.
Abbreviations: PTS = patients studies; F/U = follow-up; CR = complete response; PG = propylene glycol, PCR = partial response; NR = not reported Systemic Absorption There is no evidence of any clinically significant systemic absorption of topically applied Nitrogen Mustard. No systemic toxicities from percutaneous absorption have been observed in long-term topical Nitrogen Mustard use in MF.

Genetic toxicity—No genetic toxicity has been observed with the use of topical Nitrogen Mustard application. This is best documented in a study that demonstrated no effect on sister-chromatid exchanges in the peripheral blood lymphocytes of CTCL-MF patients assayed before and after topical Nitrogen Mustard treatment.

Bone Marrow Suppression—No evidence of bone marrow suppression (anemia, leukoopenia or thrombocytopenia) has reported with long term use of topical Nitrogen Mustard, based on serial monitoring of the complete blood count.

Heptatotoxicity—No evidence of hepatotoxicty has reported with long term use of topical NM, based on serial monitoring of peripheral blood liver function tests.

Nephrotoxicity—No evidence of nephrotoxicity has been reported with long term use of topical Nitrogen Mustard, based on serial monitoring of peripheral blood renal function tests.

Environmental Contamination

Minimal evidence of environmental contamination has been demonstrated with topical Nitrogen Mustard use.

Cutaneous Side Effects

Hyperpigmentation—resulting from the direct melanogenic effects of Nitrogen Mustard, has been reported in a large percentage of treated patients. The hyperpigmentation is reversible and decreases gradually in most patients, even if topical therapy is continued.

Contact dermatitis—is a common complication of topical Nitrogen Mustard application. An irritant contact dermatitis is most common and can be seen in up to 25% of individuals using topical Nitrogen Mustard ointment, particularly if used in sensitive areas such as the face or skin folds. Allergic contact dermatitis is also observed with topical Nitrogen Mustard use.

Immediate-type (urticarial) reactions—are rare.

Allergic contact dermatitis—from delayed-type hypersensitivity (DTH) reactions is more common and appears to be dose-dependent. Higher concentrations of aqueous preparations are associated with a DTH frequency of 10-67%. Desensitization with lower concentrations of Nitrogen Mustard has been successfully employed in patients with DTH reactions to Nitrogen Mustard. The use of a lower concentration ointment preparation dramatically reduces the incidence of DTH reactions. Stanford University reported 0% DTH reactions in patients using Nitrogen Mustard ointment for the first time and an 8% frequency of DTH in patients with a previous history of FIN hypersensitivity, in their series utilizing an Nitrogen Mustard ointment preparation.

Pediatric Use

Topical Nitrogen Mustard has been reported to be used in children and adolescences (<18 years) without any significant differences in toxicities than in adults.

Use in Pregnancy

Despite the lack of evidence of percutaneous absorption of topical Nitrogen Mustard, the use of topical Nitrogen Mustard has historically been avoided in pregnant and nursing women.

Cutaneous Carcinogenesis

There are no reports of a significantly increased incidence of squamous cell carcinoma (SCC) of the skin with prolonged use of topical Nitrogen Mustard. Several groups have reported an approximately 10% (4%-14%) frequency of SCC in CTCL-MF patients using topical Nitrogen Mustard and suggest a potential risk of epidermal carcinogenesis. These retrospective studies, however, do not account for confounding variables, such as CTCL-MF associated risk for second malignancies, prior therapies (e.g. radiation therapy to the skin), and do not have adequate control groups.

In normal DNA strand replication, a DNA strand having deoxyribonucleosides, wherein each deoxyribonucleoside may include a base adenine (A), thymine (T), cytosine (C) and guanine (G), replicates by linking each deoxyribonucleoside on the strand with another deoxyribonucleoside, wherein typical linking occurs between adenine (A) and thymine (T), forming an A-T linkage and between cytosine (C) and guanine (G), forming a C-G linkage between the original DNA strand and its replicated DNA strand.

Nitrogen Mustard alkylating agents may act as anti-cancer agents by impairing natural DNA strand replication of cancer cells, allowing unnatural base-base linkages such as a guanine (G) base linking to another guanine (G) base if the particular Nitrogen Mustard alkylating agents are bifunctional alkylators. Hereinafter, bifunctional alkylators are Nitrogen Mustards having at least two 2-chloroethyl side chains, e.g. bis-(2-chloroethyl)methyl amine, such as structure I of Reaction 1, infra.

Reaction 1, infra, depicts a reversible reaction, represented by forward reaction 1a and reverse reaction 1b in Reaction 1, in which a Nitrogen Mustard alkylating agent having a 2-chloroethyl side chain, e.g., bis-(2-chloroethyl)methylamine, represented by structure I, infra, may undergo an intramolecular cyclization, resulting in formation of a highly reactive ethyleniminium intermediate (aziridinium cation), represented by a structure II, infra. A concentration of the aziridinium cation, II, infra, may be in equilibrium with a concentration of the Nitrogen Mustard, I, infra, wherein the equilibrium constant $K_{eq(1a,1b)}$ may be represented by a ratio of a rate $k_{1a}$, of the forward reaction 1a, to a rate $k_{1b}$, of the reverse reaction 1b.

Reaction 1: Formation of Aziridinium Cation, Represented by Structure II, infra.

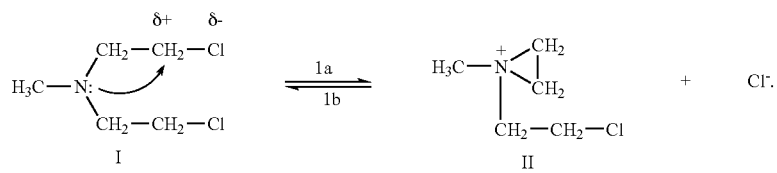

In structure I, a carbon atom bonded to chlorine may initially have a partial positive charge, δ+, and a chlorine atom may initially have a partial negative charge, δ−. In Reaction I, an unshared pair of electrons of nitrogen may form a covalent bond to the carbon having δ+, releasing the chlorine atom as chloride, and forming structure II.

Structure II, supra, may undergo nucleophilic attack by an electron donor, i.e., a nucleophile, resulting in alkylating the nucleophile. Reaction with the nucleophile guanine (G), structure III, shown in Reaction 2, supra, at position N-7 of the guanine (G) occurs to the greatest extent. Other sites on guanine (G), and other DNA bases such as adenine (A), cytosine (C) and thymine (T), and phosphate oxygens also can be alkylated. Hereinafter, structure III represents all stereoisomers and racemates of the deoxyribonucleoside having any DNA base.

In normal DNA strand replication, a DNA strand consisting of deoxyribonucleosides, wherein each deoxyribonucleoside may include a base adenine (A), thymine (T), cytosine (C) and guanine (G), replicates by linking each deoxyribonucleoside on the strand with another deoxyribonucleoside, wherein typical linking occurs between adenine (A) and thymine (T), forming an A-T linkage and between cytosine (C) and guanine (G), forming a C-G linkage between the original DNA strand and its replicated DNA strand.

Nitrogen Mustard alkylating agents may act as anti-cancer agents by impairing normal DNA strand replication, allowing Reaction 2: Nucleophilic attack by guanine on the unstable aziridinium ring, structure II, resulting from the intramoecular cyclization shown in Reaction 1, supra.

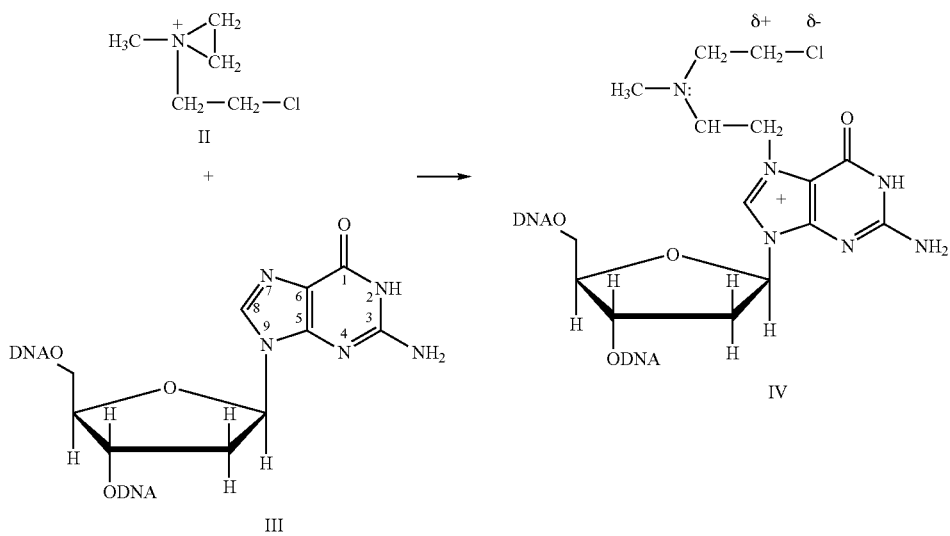

Reaction 2 results in forming the alkylated deoxyribonucleoside, structure IV. In Reaction 2 supra, position N-7 of the guanine (G) base of the deoxribonucleoside, represented in structure III, may nucleophilically attack the aziridinium ring, structure II, that may have been formed by the intramolecular cyclization represented by Reaction 1, supra, resulting in alkylating position N-7 of the guanine (G) base of structure III. Hereinafter, structure IV represents all stereoisomers and racemates of the deoxyribonucleoside having any DNA base.

Alkylating agents have four actions on nucleic acids. First of all, the agent may cause crosslinking of DNA strands which interferes with DNA and RNA synthesis. This is thought to be the most important reason for the cytotoxic effect of alkylating agents. Secondly, the agent may alter the "side chain groups" of the nucleotide base ring which would lead to abnormal base pairing and point mutations in the synthesized DNA and RNA chains. Thirdly, the alkylating agent may split the base ring from the nucleotide which again interrupts proper DNA and RNA synthesis. Finally, the alkylating agent may break the ring structure of a nucleotide base which would prevent base pairing during DNA and RNA synthesis.

abnormal base-base linkages such as a guanine (G) base linking to another guanine (G) base if the particular Nitrogen Mustard alkylating agents are bifunctional alkylators. Hereinafter, bifunctional alkylators are Nitrogen Mustards having at least two 2-chloroethyl side chains, e.g. bis-(2-chloroethyl) methyl amine, structure I, supra.

In Reaction 2, supra, one of the 2-chloroethyl side chains of the deoxyribonucleoside represented by the structure IV has alkylated the guanine (G) base of the structure III. In reversible Reaction 3, infra, the remaining 2-chloroethyl side chain of the deoxyribonucleoside of the structure IV has also undergone an intramolecular cyclization, resulting in formation of deoxyribonucleoside V, having the highly reactive aziridinium ring.

Reaction 3: Formation of Aziridinium Cation from the remaining 2-chloroethyl side chain of the deoxyribonucleoside of the structure IV, supra.

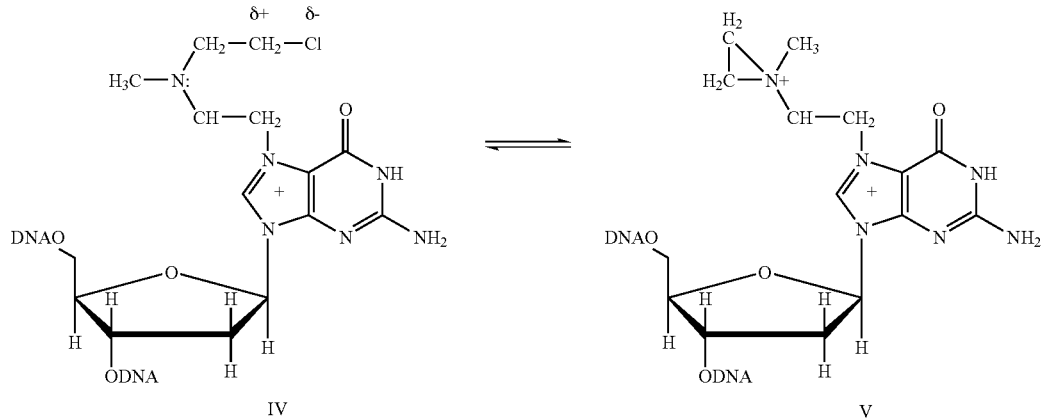

Reaction 4, infra, depicts the abnormal linking of the deoxyribonucleoside V, having a guanine (G) base and the activated aziridinium ring, with another deoxyribonucleoside III, also having a guanine (G) base, forming an abnormal guanine-guanine (G-G) link in the product, represented by the somersstructure VI. Hereinafter, structure VI represents all stereoi and racemates of the product from coupling two molecules of the deoxyribonucleoside represented by structure III at the N-7 position with the bifunctional alkylating Nitrogen Mustard represented by the structure II, supra.

Reaction 4: The Abnormal Linking of the Deoxyribonucleoside V, Having a Guanine (G) Base And The Activated Aziridinium Ring, With Another Deoxyribonucleoside VI, Also Having a Guanine (G) Base.

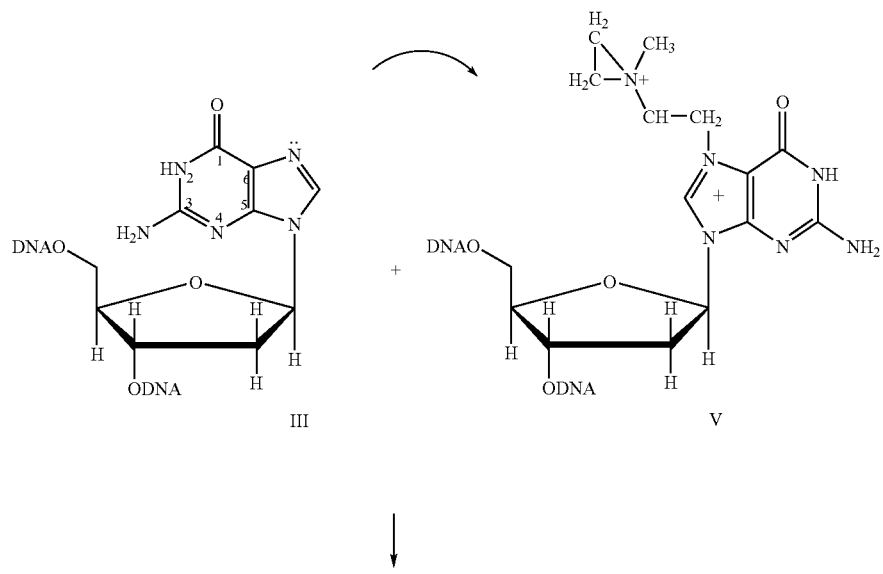

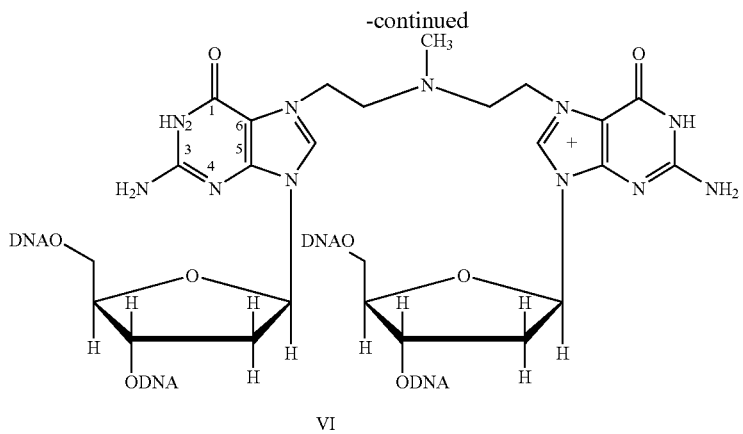

VI

A highly unstable nature and extremely short duration of action of the Nitrogen Mustards in the presence of water may result because water may decompose the highly reactive ethyleniminium intermediate (aziridinium cation), represented by the structure II, in Reaction 1, supra, replacing the chlorine atom on the 2-chloroethyl side chains of the Nitrogen Mustard by an OH group. The Nitrogen Mustards are said to be highly unstable and have an extremely short duration of action because they may react with water, resulting in replacement of one or both of the chlorine atoms by a hydroxyl (OH) group. Replacement of the chlorine atoms may block formation of the aziridinium cation and therefore may prevent the Nitrogen Mustards from acting as alkylating agents of, for example, the N-2 position of the guanine base of DNA. Reaction 5 illustrates competing equilibrium reactions, 1a and 1b and 5a and 5b. In Reactions 1a and 1b, a free form of the Nitrogen Mustard, structure I, may be in equilibrium with the aziridium ion II, as described for Reaction 1, supra. The equilibrium constant for Reactions 1a and 1b has been described as $K_{eq(1a,1b)}$, supra. In like manner, the equilibrium constant for Reactions 5a and 5b, $K_{eq(5a,5b)}$ may be expressed as the ratio of the concentration of the HX salt, IX, to the product of the concentration of the free form of the Nitrogen Mustard, structure I and the concentration of HX. Therefore, in an embodiment, there may be an equilibrium concentration of aziridinium cation represented by the ratio of $K_{eq(1a,1b)}$ to $K_{eq(5a,5b)}$, even when the Nitrogen Mustard has been stabilized by converting the free base form of the Nitrogen Mustard, as represented by structure I, infra, as illustrated by Reaction 5, infra, to its HX salt, as represented by the structure IX. Therefore, the N-2 position of the guanine base of DNA, structure III in Reactions 2-4 may be alkylated by the HX salt IX, as in Reaction 5, infra, because the concentration of the aziridinium cation in Reaction 5, infra, may be a real positive number, equal to $K_{eq(1a,1b)}$ to $K_{eq(5a,5b)}$. Hereinafter, the free base form of the Nitrogen Mustard is any non-salt form of the Nitrogen Mustard, wherein a lone pair of electrons on the nitrogen atom may be available for forming the aziridinium ion, II, as in Reaction 1, supra. In embodiments of the present invention, the aziridinium cation, Structure II, supra, may undergo nucleophilic attack by an electron donor, resulting in alkylating the nucleophile. For example, reaction with the nucleophile guanine (G), structure III, shown in Reaction 2, at position N-7 of the guanine (G) occurs to the greatest extent. Other sites on guanine (G), and other DNA bases such as adenine (A), cytosine (C) and thymine (T), and phosphate oxygens also can be alkylated.

The inventors disclose that oxygen of primary alcohols often are nucleophiles and therefore may have a disadvantageous effect on the use of the free base or the pharmaceutically acceptable HX salt IX, as in reaction 5, infra, because the free base of the nitrogen mustard or the pharmaceutically acceptable HX salt IX is consumed in the undesirable side reaction in which the nucleophile is alkylated by the free base of the nitrogen mustard or the pharmaceutically acceptable HX salt IX, instead of being available to act as an anti-cancer agent against T-Cell lymphoma, for example, by impairing normal DNA strand replication. Hereinafter, pharmaceutically acceptable HX salt IX, as in reaction 5, infra, refers to salt forms that are pharmacologically acceptable and substantially non-toxic to the subject being treated with the compound of the invention. Therefore, secondary and tertiary alcohols, amines, amino alcohols having from 1 to 20 carbon atoms and polypropylene glycol (PPG, molecular weight from about 300 to about 2500), propylene glycol (PG,), polyethyleneglycol (PEG, molecular weight from about 100 to about 5000), 2-(2-ethoxyethoxy) ethanol, or ethylene glycol are preferred over petrolatum, ethyl alcohol or water in formulations of the free base of the nitrogen mustard or the pharmaceutically acceptable HX salt IX, when a pharmaceutically acceptable inert ingredient, i.e., a pharmaceutically acceptable excipient, may be needed to promote solubilization of the free base of the nitrogen mustard or the pharmaceutically acceptable HX salt IX in the non-aqueous vehicle or carrier that does not include petrolatum or ethanol.

Ethyl alcohol is not used to dissolve the nitrogen mustard or its HX salt because it is a nucleophile that degrades the nitrogen mustard or its HX salt by promoting loss of chlorine. Isopropyl, cetyl, stearyl, cetearyl, or lanolin alcohol are preferred pharmaceutically acceptable excipients for dissolving or taking up the nitrogen mustard or its HX salt. Alternatively, for example, for topical formulations, pharmaceutically acceptable excipients may comprise solvents, emollients, humectants, preservatives, emulsifiers, and pH agents. Suitable solvents include acetone, glycols, polyurethanes, and others known in the art. Suitable emollients include mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Alternatively, pH agents include from about 1 percent by weight to about 15 percent by weight acetic acid, citric acid, tartaric acid, fumaric acid, lactic, glycolic and other alpha hydroxy acids, malic acid, carnitine, glutamic acid, aspartic acid and others known in the art. Suitable preservatives include benzyl alcohol, sodium benzoate, parabens, and others known in the art.

The inventors report that polyethylene glycol (PEG), ethylene glycol (EG), polypropylene glycol (PPG), propylene glycol (PG) and the diethylene glycol monosubstituted ether, polypropylene glycol (PPG, molecular weight from about 300 to about 2500), propylene glycol (PG,), polyethyleneglycol (PEG, molecular weight from about 100 to about 5000) or ethylene glycol are useful pharmaceutically acceptable excipients. The polyethylene glycol (PEG), ethylene glycol (EG), polypropylene glycol (PPG), propylene glycol (PG) and the diethylene glycol monosubstituted ether that may hydrogen bond to trace nucleophiles that may be contaminants in the pharmaceutically acceptable excipients, thereby reducing the nucleophilic strength of the trace nucleophiles. Therefore diethylene glycol monosubstituted ether or silicones such as dimethicone or cyclomethicone are useful as pharmaceutically acceptable excipients to promote dissolution of the free base of the nitrogen mustard or the HX salt IX, infra, in formulations of the free base of the nitrogen mustard or the pharmaceutically acceptable HX salt IX, infra.

In embodiments of the present invention, pharmaceutically acceptable HX salts of the Nitrogen Mustard, structure IX, infra, are more stable and of longer activity duration than their respective free bases, as measured by an effective alkylating activity of the pharmaceutically acceptable HX salts of the Nitrogen Mustard, structure IX, infra, in the non-aqueous vehicle or carrier that does not include petrolatum or ethanol, wherein an effective alkylating activity of the pharmaceutically acceptable HX salts in the non-aqueous vehicle or carrier that does not include petrolatum or ethanol after three (3) years is equivalent to the effective alkylating activity of the free base form of the respective Nitrogen Mustards, structure I, after 3 months in the non-aqueous vehicle or carrier that does not include petrolatum or ethanol. The non-aqueous vehicle or carrier that does not include petrolatum or ethanol in formulations of the nitrogen mustard free base or the pharmaceutically acceptable HX salts, structure IX, infra, does not include any grade of white or yellow petrolatum recognized in the art as suitable for human application. The non-aqueous vehicle or carrier that does not include petrolatum or ethanol does not include material commercially available as Penreco Snow White Pet USP in formulations of the nitrogen mustard free base or the pharmaceutically acceptable HX salts, structure IX, infra. The non-aqueous vehicle or carrier that does not include petrolatum or ethanol does not include hydrocarbon mixtures formulated with mineral oils in combination with paraffin waxes of various melting points in formulations of the nitrogen mustard free base or the pharmaceutically acceptable HX salts, structure IX, infra. The non-aqueous vehicle or carrier that does not include petrolatum or ethanol does not include a lipophilic emollient selected from the group consisting of: petrolatum; esters of fatty acids. Hereinafter, the effective alkylating activity of the pharmaceutically acceptable HX salts, structure IX, infra, in the non-aqueous vehicle or carrier that does not include petrolatum or ethanol is equivalent to the effective alkylating activity of the free base form of the respective Nitrogen Mustards in the non-aqueous vehicle or carrier that does not include petrolatum or ethanol when a weight percent of the pharmaceutically acceptable HX salt, structure IX, infra, in the non-aqueous vehicle or carrier that does not include petrolatum or ethanol is essentially equal to the weight percent of the respective free base of the Nitrogen Mustard, structure I in the non-aqueous vehicle or carrier that does not include petrolatum or ethanol.

In embodiments of the present invention, use of the pharmaceutically acceptable HX salt, structure IX, infra, of the Nitrogen Mustard in the non-aqueous vehicle or carrier that does not include petrolatum or ethanol may preserve the effective alkylating activity by reducing its volatility compared to that of the free base form, since pharmaceutically acceptable HX salts of Nitrogen Mustards generally have lower vapor pressures than their corresponding free base forms.

Reaction represented by arrow 5c, infra, illustrates formation of the stabilized Nitrogen Mustard.HX compositions of the present invention that have been stabilized by converting said free form highly reactive Nitrogen Mustard alkylating agents to pharmaceutically acceptable HX salts by reaction of the Nitrogen Mustard with HX.

Reaction 5: Formation of Nitrogen Mustard • HX, Represented by Structure IX, wherein the Nitrogen Mustard is Represented by Structure I, as in Reaction 1, supra..

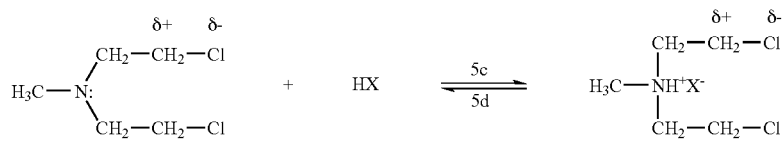

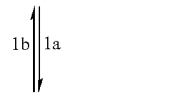

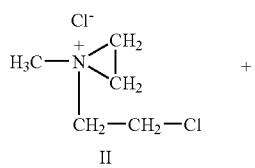

In an embodiment, $X^-$ may advantageously be halide, such as $Cl^-$, $Br^-$, $I^-$ or $HSO_4^-$ or $NO_3^-$, wherein HX may be respectively, HCl, HBr, HI, or $H_2SO_4$, or $HNO_3$. Alternatively pharmaceutically acceptable HX salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

FIG. 1 depicts an embodiment of the present invention, a method 1, for treating a person with a skin disorder, comprising: a step 10, topically applying to the affected skin a Nitrogen Mustard or a pharmaceutically acceptable HX salt of the Nitrogen Mustard, wherein the Nitrogen Mustard or the pharmaceutically acceptable HX salt of the Nitrogen Mustard is in a non-aqueous vehicle or carrier that does not include petrolatum or ethanol, wherein the Nitrogen Mustard is represented by the following structures:

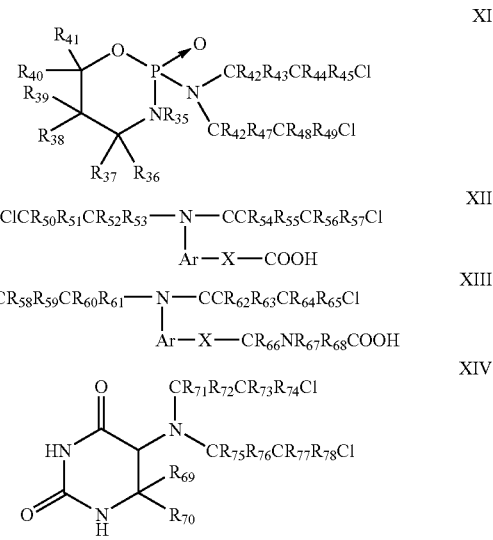

wherein each $R_1$, $R_2$, $R_3$ ... $R_{34}$ ($R_1$-$R_{34}$) is independently selected from the group consisting of H, a linear alkyl group having 1-6 carbon atoms, a branched alkyl group having 2-12 carbon atoms, a cycloalkyl group having 3-17 carbon atoms, a fluorinated linear alkyl group having from 2-12 carbon atoms, a fluorinated branched alkyl group having 2-12 carbon atoms, a fluorinated cycloalkyl group having 3-17 carbon atoms, aryl groups, aralkyl groups, alkaryl groups, cycloalkyl groups, bicycloalkyl groups, alkenyl groups, alkalkenyl groups, alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups, alkylenylacyl groups and alkynylacyl groups, wherein n is 1, 2, . . . 3, wherein p is 0, 1, . . . 2, wherein n+p≦3, and wherein any two $R_1$-$R_{34}$ in the same molecule may be linked to form a three- to eight-membered cyclic group.

In an embodiment, the Nitrogen Mustard is advantageously selected from the group consisting of bis-(2-chloroethyl)ethylamine, bis-(2-chloroethyl)methylamine, and tris-(2-chloroethyl)amine, and combinations thereof. Hereinafter, structures VII, VIII, IX and X (XI-XIV) may represent all racemic forms and stereoisomers wherein said compounds may be capable of optical activity.

Alternatively, in an embodiment, the Nitrogen Mustard may be advantageously derived from a Nitrogen Mustard prodrug represented by the following structures:

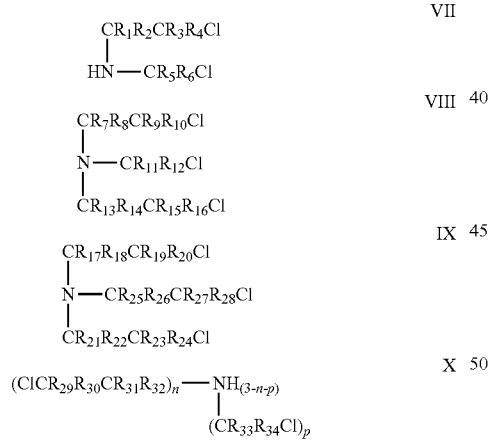

wherein each $R_{35}$, $R_{36}$, $R_{37}$ ... $R_{78}$ ($R_{35}$-$R_{78}$) is independently selected from the group consisting of H, linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, aryl groups, aralkyl groups, alkaryl groups, cycloalkyl groups, bicycloalkyl groups, alkenyl groups, alkalkenyl groups, and alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups alkylenylacyl groups and alkynylacyl groups, and wherein any two $R_1$-$R_{57}$ in the same molecule may be linked to form a three- to eight-membered cyclic group, wherein each X group is a linking group selected from the group consisting of linear or branched alkylene having 1 to 7 carbon atoms, cycloalkylene having 3 to 17 carbon atoms, alkylcycloalkylene having 4 to 20 carbon atoms, a cycloalkylalkylene having 4 to 20 carbon atoms, an arylene, having 4 to 30 carbon atoms, an alkylarylene, having 4 to 30 carbon atoms, an arylalkylene, having 4 to 30 carbon atoms, and combinations thereof, wherein each Ar group is a bifunctional aromatic linking group wherein each Ar is selected from the group consisting of arylene, substituted arylene and/or heteroarylene.

Compounds represented by structures XI, XII, . . . XIV (XI-XIV) may be prodrug candidate forms of the Nitrogen Mustards, because they can be metabolized in vivo to generate the active Nitrogen Mustard. Hereinafter, a "prodrug" is a precursor (forerunner) of the active Nitrogen Mustard. A prodrug may undergo chemical conversion by metabolic processes to the parent drug, thus becoming an active Nitrogen Mustard. Hereinafter, structures XI, XII, . . . XIV (XI-XIV) may represent all racemic forms and stereoisomers wherein said compounds may be capable of optical activity.

For example, phosphatase and phosphamidase enzymes may hydrolyze the P-N bond of structure XI, supra,e.g., cyclophosphamide, structure XIA, infra or ifosphamide, structure XIB, infra, resulting in an intermediate aldophosphamide, which may nonenzymatically break down to a bifunctional phosphoramide mustard. In an embodiment, cyclophosphamide, structure XIA, supra or ifosphamide, structure XIB, supra may be oxidatively activated by cytochrome P-450

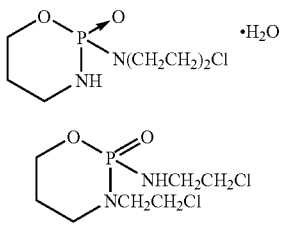

XIA

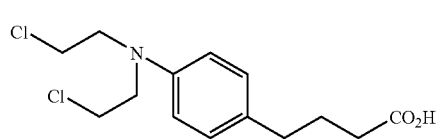

XIB

In an embodiment, structure XII, supra, e.g., Chlorambucil, structure XIIA, infra, may be a bifunctional alkylating agent of the nitrogen mustard type.

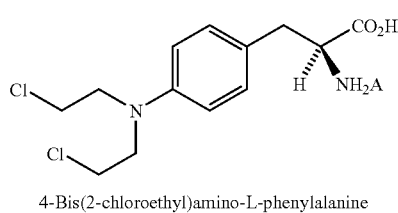

XIIA

Structure XII may be cell cycle-phase nonspecific, although it also may be cytotoxic to nonproliferating cells. Activity may occur as a result of formation of an unstable ethylenimmonium ion, which alkylates or binds with many intracellular molecular structures, including nucleic acids. Its cytotoxic action may be primarily due to cross-linking of strands of DNA, which inhibits nucleic acid synthesis In an embodiment structure, XIII, supra, e.g., Melphalan, structure XIIIA, infra, may be a bifunctional alkylating agent of the nitrogen mustard type.

XIIIA

4-Bis(2-chloroethyl)amino-L-phenylalanine

Like the nitrogen mustard prodrugs of structure XII, prodrugs of structure XIII may be cell cycle-phase nonspecific, although they also may be cytotoxic to nonproliferating cells.

In an embodiment, structure XIV, supra, e.g., uracil mustard, structure XIVA, infra, may be a bifunctional alkylating agent of the nitrogen mustard type.

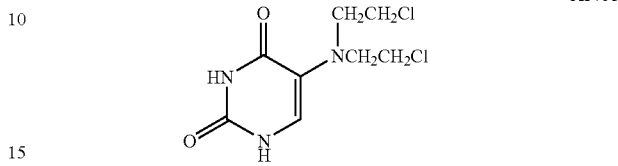

XIVA

In an embodiment, the pharmaceutically acceptable HX salt of the Nitrogen Mustard may be advantageously selected from the group consisting of Nitrogen Mustard.HCl, Nitrogen Mustard.H$_2$SO$_4$, Nitrogen Mustard.HNO$_3$, Nitrogen Mustard.H$_2$SO$_4$, Nitrogen Mustard.HBr, Nitrogen Mustard.HI and combinations thereof.

In an embodiment, an ingredient of the non-aqueous vehicle or carrier that does not include petrolatum or ethanol may be selected from the group consisting of polyethylene glycol (PEG) or ethylene glycol (PEG), polypropylene glycol (PPG) or propylene glycol (PG), diethylene glycol monomethyl ether (DGME), HOCH$_2$CH$_2$OCH$_2$CH$_2$OR$_{79}$ (HO(CH$_2$CH$_2$O)$_2$R$_{79}$), wherein R$_{79}$ is selected from the group consisting of a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group and an alkynylacyl group, and combinations thereof. In an embodiment, each ingredient of the non-aqueous vehicle or carrier that does not include petrolatum or ethanol may be selected from the group consisting of Ethoxy Diglycol Reagent, Hydroxypropylcellulose, Menthol Crystals USP, Butylated Hydroxytoluene NF, Glycerin USP, Edetate Disodium USP, Decyl Methyl Sulfoxide, Kris-Ester 236 and combinations thereof.

In an embodiment, pharmaceutically acceptable HX salts of the Nitrogen Mustard alkylating agents used in the treatment of skin disorders may be more stable and have a longer duration of activity because the pharmaceutically acceptable HX salts of the Nitrogen Mustards may be more resistant to attack by water than the respective free base form of the Nitrogen Mustard. In an embodiment, the pharmaceutically acceptable HX salts of the Nitrogen Mustard alkylating agents may be added to a non-aqueous vehicle or carrier that may not include petrolatum. In an embodiment, the use of pharmaceutically acceptable HX salts of the Nitrogen Mustard alkylating agents and/or adding them to the non-aqueous vehicle or carrier that may not include petrolatum may result in greater stability and longer duration of action in the treatment of skin disorders.

In an embodiment, the skin disorder is selected from the group consisting of psoriasis, eczema, actinic keratosis, lupus, sarcoidosis, alopecia, cutaneous T-Cell lymphoma, i.e., mycosis fungoides, lymphoreticular neoplasia, pleural and peritoneal effusions, cutaneous B-cell lymphoma, pseudolymphomas of the skin, squamous cell carcinoma, basal cell carcinoma, bronchogenic carcinoma, malignant melanoma, lymphosarcoma, chronic lymphocytic leukemia, polycythemia vera, lymphomatoid papulosis, Mucha-Habberman's disease (PLEVA), vitiligo, and combinations thereof.

The rationale for the use of topical NM for the treatment of vitiligo lies in the clinical and experimental observations that NM produces cutaneous hyperpigmentation not associated with an inflammatory response. It has long been observed that the treatment of MF with topical NM produces hyperpigmantation. The same phenomenon has been reported in NM treatment of psoriasis. Indeed, the inventors disclose successful regimentation of vitiligo treated with topical NM has been demonstrated. Supporting the direct effect of NM on melanogenesis, the pigmentation of hairless mice in response to topical NM. In humans, ultra structure studies demonstrate topical NM increases melanosome numbers and distribution without toxic effects to epidermal microenvironment.

Methods of delivery, as in the step 10 of the method 1 comprise topical administration of the Nitrogen Mustard or Nitrogen Mustard.HCl to humans and animals of sterile solutions or suspensions, wherein the dosage contains suitable quantities of an active ingredient. Topical solutions or suspensions are incorporated in a slow release non-aqueous matrix for administering transdermally. In an embodiment, a dosage for mammals may be from about 0.0001 percent by weight to about 2.0 percent by weight of the active ingredient in the non-aqueous and non-petrolatum matrix per day. In another embodiment, the dosage for mammals may be from about 0.015 percent by weight to about 0.04 percent by weight of the active ingredient in the non-aqueous and non-petrolatum matrix per day. In an embodiment, the dosage for mammals may be from about 0.015 to about 0.030 percent by weight of the active ingredient in the non-aqueous and non-petrolatum matrix per day. Hereinafter, topical administration means applying a drug to a localized area of the body or to the surface of a body part.

In embodiments of the present invention, a method for treating a person with a skin disorder, comprising: topically applying the Nitrogen Mustard or Nitrogen Mustard.HCl to the affected skin. In an embodiment of the method, the non-aqueous vehicle or carrier that does not include petrolatum or ethanol ameliorates skin irritation resulting from the Nitrogen Mustard or its HX salt, by providing an effective dose of the Nitrogen Mustard or Nitrogen Mustard.HCl. Hereinafter, "ameliorates" means to lessen pain and reduce skin irritation, resulting in making an improvement because skin irritation has been reduced. Hereinafter, an effective dose of the Nitrogen Mustard or Nitrogen Mustard.HCl may be sufficient to treat the skin having one of the aforementioned diseases without causing hypersensitivity, as disclosed in Table 1, supra.

In embodiments of the present invention, a method for stabilizing a volatile alkylating agent, comprising: providing a non-aqueous flowable ointment or cream, wherein the non-aqueous flowable ointment or cream does not include petrolatum or ethanol; reconstituting an HX salt of the volatile alkylating agent in solvent that does not include ethanol; combining with mixing the non-aqueous flowable ointment or cream and the HX salt of the volatile alkylating agent. In an embodiment, in the method for stabilizing the Nitrogen Mustard or Nitrogen Mustard.HCl, the HX salt of the Nitrogen Mustard is Nitrogen Mustard.HCl. In an embodiment of the method for stabilizing the Nitrogen Mustard or the Nitrogen Mustard.HCl, a duration of activity of the Nitrogen Mustard or the HX salt of the Nitrogen Mustard is from about 3 months to about 3 years.

In an embodiment, in the method for stabilizing the Nitrogen Mustard or the Nitrogen Mustard.HCl, the non-aqueous flowable ointment or cream includes polypropylene glycol (PPG), propylene glycol (PG) or polyethylene glycol (PEG) or ethylene glycol (EG). In an embodiment, in the method for stabilizing the Nitrogen Mustard or the Nitrogen Mustard.HCl, the non-aqueous flowable ointment or cream consists essentially of Propylene Glycol, Ethoxy Diglycol Reagent, Hydroxypropylcellulose, Menthol Crystals USP, Butylated Hydroxytoluene NF, Glycerin USP, Edetate Disodium USP, Decyl Methyl Sulfoxide, and Kris-Ester 236.

In an embodiment, in the method for stabilizing the Nitrogen Mustard or the Nitrogen Mustard.HCl, the Nitrogen Mustard or its HX salt is selected from the group consisting of bis-(2-chloroethyl)ethylamine, bis-(2-chloroethyl)methylamine, tris-(2-chloroethyl)amine, and combinations thereof.

In one embodiment, the acceptable non-aqueous vehicle or carrier that does not include petrolatum or ethanol for the purpose of this invention may be flowable non-aqueous pharmaceutical vehicle or carriers such as creams or ointments that do not contain nucleophiles, e.g., water or ethanol, that may decompose the Nitrogen Mustard or its HX salt, structure IX, as depicted in Reaction 5, supra. In an embodiment, suitable pharmaceutically acceptable carriers include Ethoxy Diglycol Reagent, Hydroxypropylcellulose, Menthol Crystals USP, Butylated Hydroxytoluene NF, Glycerin USP, Edetate Disodium USP, Decyl Methyl Sulfoxide, Kris-Ester 236, Propylene glycol and Ethylene Glycol. In an embodiment, the polypropylene glycol (PPG), propylene glycol (PG), polyethylene glycol (PEG) or ethylene glycol (EG) may be from about 15 to about 60 weight percent propylene glycol or ethylene glycol. The non-aqueous vehicle or carrier that does not include petrolatum or ethanol may also contain adjuvants such as preserving, stabilizing, wetting, emulsifying agents and the like together with the sensitizer of this invention.

In an embodiment of the present invention, the sensitizers can also be used as adjunct therapy in combination with existing therapies, such as hyperthermia, in the management cancer treatment in patients having cancer.

EXAMPLE 1

Preparation of a Topical Ointment From About 0.001 to About 2.0 Parts by Weight Bis-(2chloroethyl)methylamine Hydrochloride, structure IX, as depicted in Reaction 5 supra, per 100 Parts by Weight of a Pharmaceutically Acceptable Nitrogen Mustard Hydrochloride in a Pharmaceutically Acceptable Vehicle or Carrier The topical ointment comprises a pharmaceutically acceptable nitrogen mustard hydrochloride in a pharmaceutically acceptable vehicle or carrier, wherein the pharmaceutically acceptable vehicle or carrier does not include petrolatum or ethanol. The components/composition are provided in Table 2 that follows.

TABLE 2

Unit/Batch Composition

| Ingredient | Amount per 100 ml | Per Batch[a] | Percent |
|---|---|---|---|
| PPG, PG, PEG or EG USP | 15-60 ml | 0.15-0.6 L | 15-60% |
| Ethoxy Diglycol Reagent | 15-60 ml | 0.15-0.6 L | 15-60% |
| Hydroxypropylcellulose NF 1500 CPS | 0.75 gm | 0.0075 kg | 0.75% |
| Menthol Crystals USP | 0.08 gm | 0.0008 kg | 0.08% |
| Butylated Hydroxytoluene NF (BHT) | 0.05 gm | 0.0005 kg | 0.05% |
| Glycerin USP | 12.75 ml | 0.1275 L | 12.75% |
| Edetate Disodium USP | 0.05 gm | 0.0005 kg | 0.05% |
| Decyl Methyl Sulfoxide | 0.125 gm | 0.00125 kg | 0.13% |
| Kris-Ester 236 liquid | 5 gm | 0.05 kg | 5.00% |
| Alchohol Anydrous 100% SDA 3A | 2.175 ml | 0.02175 L | 2.18% |
| Bis-(2-chloroethyl)methyl-amine HCl[b] | 0.001-2.0 gm gm | 0.00001-0.02 kg | 0.001-2.0% |

[a]Slight overages of the drug substances may be used as required to offset losses during manufacture.
[b]Availble from Merck & Co., West Point, PA 19486.

Manufacturing

The topical ointment, e.g., having 0.001 -2.0 percent by weight Nitrogen Mustard as Bis-(2chloroethyl)methylamine-.HCl, structure IX, as in Reaction 5, supra, may be manufactured according to the following general procedure:

Preparation of the Ointment

1. All dry excipient ingredients are assembled and weighed out according to the formula in Table 2 and placed in an appropriate vessel. Hereinafter, an excipient is an inert substance which is added to the free form of the nitrogen mustard or its pharmaceutically acceptable HX salt to provide bulk. Hereinafter, the dry excipient ingredients are indicated as being added as solid weight, such as gram, i.e. gm.
2. Particle sizes of the dry material are reduced to a uniform size through tritration.
3. Polypropylene glycol (PPG), propylene glycol (PG), polyethylene glycol (PEG) or ethylene glycol (EG) from about 15 to about 60 percent by weight is then added via the principle of geometric dilution to form a smooth paste. Once a smooth paste is achieved, the propylene or ethylene glycol continues to be added until a volume that retains a flow like quality is obtained.
4. The entire contents are then transferred to a large beaker. A spin bar is added and the beaker is placed on a magnetic stirring plate and mixing is begun.
5. As the mixture continues to spin, glycerin is added. While the mixture spins, the original vessel is washed with from about 15 to about 60 percent by weight ethoxy digycol and the contents of the vessel are added to the spinning mixture in the beaker.
6. After the ethoxy diglycol is added, kris-ester is added to the spinning mixture. This mixture then is spun for approximately one to two hours. After the spinning is finished the mixture is covered and left to sit over-night.
7. The next day the mixture is mixed with a high shear mixer to a uniform consistency with minimal to no air. Air and moisture may be removed during mixing by applying a vacuum from about 0.01 to about 0.1 torr. The mixture is then brought to ambient pressure by adding dry nitrogen.

Adding the Nitrogen Mustard

8. The appropriate concentration and amount of Nitrogen mustard is reconstituted with absolute alcohol (200 proof) then added to the appropriate amount of non-aqueous vehicle or carrier, wherein the non-aqueous vehicle or carrier does not include petrolatum or ethanol and mixed to a uniform consistency via agitation for 60-90 seconds For example, in an embodiment, a concentration in mg/ml of the pharmaceutically acceptable Nitrogen Mustard.HCl in the non-aqueous vehicle or carrier that does not include petrolatum or ethanol is advantageously from about 1 mg of Nitrogen Mustard.HCl per 100 ml of non-aqueous vehicle to about 2000 mg of Nitrogen Mustard.HCl per 100 ml of non-aqueous vehicle. In an embodiment, a concentration in mg/ml of Nitrogen Mustard.HCl in a non-aqueous vehicle or carrier that does not include petrolatum or ethanol is advantageously from about 10 mg of Nitrogen Mustard.HCl per 100 ml of non-aqueous vehicle or carrier that does not include petrolatum or ethanol to about 40 mg of Nitrogen Mustard.HCl per 100 ml of non-aqueous vehicle or carrier that does not include petrolatum or ethanol. In an embodiment, a concentration in mg/ml of Nitrogen Mustard.HCl used in a non-aqueous vehicle or carrier that does not include petrolatum or ethanol is advantageously from about 15 mg of Nitrogen Mustard.HCl per 100 ml of non-aqueous vehicle or carrier that does not include petrolatum or ethanol to about 30 mg of Nitrogen Mustard.HCl per 100 ml of non-aqueous vehicle or carrier that does not include petrolatum or ethanol.

9. This mixture is then poured into a 50 ml flip top plastic cylinder and shipped to the appropriate patient.

Clean-up

All vessels used in the process are placed in a Sodium Thiosulfate-Sodium Bicarbonate aqueous bath. Contents are left in the bath for 2 hours and then the washed. The bath is then discarded by normal means. Note: Sodium Thiosulfate reacts with nitrogen mustard to create an innocuous, safe mixture that can be discarded by normal means.

EXAMPLE 2

Preparation of a Topical Ointment From About 0.001 to About 2.0 Parts by Weight Bis-(2chloroethyl)methylamine Hydrochloride, structure IX, as depicted in Reaction 5 supra, in a Pharmaceutically Acceptable Nitrogen Mustard Hydrochloride in a Pharmaceutically Acceptable Vehicle or Carrier per 100 Parts by Weight of the Topical Ointment The drug product formulation comprises a pharmaceutically acceptable nitrogen mustard hydrochloride in a pharmaceutically acceptable vehicle or carrier in a topical ointment base. The components/composition are provided in Table 3 that follows.

TABLE 3

Unit/Batch Composition

| Ingredient[a] | Parts per 100 Parts by Weight of a Topical Ointment |
|---|---|
| Dimethicone, Cyclomethicone, or HO(CH$_2$CH$_2$O)$_2$R$_{79}$) | 10-60 |
| Ethoxy Diglycol Reagent | 10-16 |
| Hydroxypropylcellulose NF 1500 CPS | 0-5 |
| Menthol Crystals USP | 0-1 |
| Butylated Hydroxytoluene NF (BHT) | 0-1 |
| Glycerin USP | 1-2 |
| Edetate Disodium USP | 0-0.05 |
| Decyl Methyl Sulfoxide | 0-0.125 |
| Kris-Ester 236 liquid | 0-5 |
| Anydrous Secondary or tertiary Alcohol | 1-20 |
| Bis-(2-chloroethyl)methylamine HCl[b] | 0.001-2.0 |
| C$_n$H$_{(2n+2)}$COOH, (n = 1-6) | 0.01-15 |

[a] Slight overages of the drug substances may be used as required to offset losses during manufacture.
[b] Availble from Merck & Co., West Point, PA 19486.

The acceptable non-aqueous vehicle or carrier that does not include petrolatum or ethanol for the purpose of this invention that is the flowable non-aqueous pharmaceutically acceptable non-aqueous vehicle or carrier that does not include petrolatum or ethanol such as creams or ointments do not contain nucleophiles, e.g., water or ethanol, that may decompose the free form of the Nitrogen Mustard or its HX salt, structure IX, as depicted in Reaction 5, supra, may be dimethyl polysiloxane fluid such as dimethicone or cyclomethicone having essentially no moisture content.

Hereinafter dimethicone means low viscosity silicones, low viscosity, i.e. from about 1 cps. to about 1,000 cps at 25° C. polydimethylsiloxanes, Hexamethyldisiloxane, CAS# 107-46-0, pure silicone 1 cSt, volatile silicone, volatile silicones, volatile polydimethylsiloxanes, low temperature silicones, skin care silicone, skin care silicones, Octamethyltrisiloxane, CAS# 107-51-7, CAS107-51-7, Decamethyltetrasiloxane, (CAS# 141-62-8, Dodecamethylpentasiloxane CAS# 141-63-9, trisiloxane, low viscosity dimethicone, volatile dimethicone, cosmetic dimethicone fluid, cosmetic base fluids, suntan lotion silicone, antiperspirant silicone, hair care silicone, low surface tension silicone, and low heat of vaporization silicone.

Hereinafter, cyclomethicone means cyclopentasiloxane, volatile poydimethylcyclosiloxane, CAS 541-02-6, CAS# 541-02-6, low surface tension silicone, volatile silicone, D5 silicone, Dow Corning 245 fluid, DC 245 fluid, 245 silicone, skin cream silicone, antiperspirant silicone, suntan lotion silicone, silicone for skin, skincare silicone, bodycare silicone, bath oil silicone, GE 1202, GE SF1202 cyclopentasiloxane, D5 Cyclopentasiloxane, and D5 Decamethylcyclo Pentasiloxane.

Generally, dimethicone and cyclomethicone are dimethyl silicone oils with good emollience, strong moisturization and humectant properties. Dimethicone and cyclomethicone have very low moisture content, as water, i.e. <0.1% by weight because they are methyl stopped instead of OH stopped polymers.

Manufacturing

The drug product, e.g., having 0.001-2.0 percent by weight Nitrogen Mustard as Bis-(2chloroethyl)methylamine.HCl, structure IX, as in Reaction 5, supra, in Dimethicone or Cyclomethicone Ointment may be manufactured according to the following general procedure:

Preparation of the Dimethicone or Cyclomethicone Ointment a) All dry excipient ingredients are assembled and weighed out according to the formula in Table 3 and placed in an appropriate vessel.
b) Particle sizes of the dry material are reduced to a uniform size through tritration.
c) Dimethicone or cyclomethicone from about 10 to about 60 percent by weight is then added via the principle of geometric dilution to form a smooth paste. Once a smooth paste is achieved, the Dimethicone or cyclomethicone continues to be added until a volume that retains a flow like quality is obtained.
d) The entire contents are then transferred to a large beaker. A spin bar is added and the beaker is placed on a magnetic stirring plate and mixing is begun.
e) As the mixture continues to spin, glycerin is added. While the mixture spins, the original vessel is washed with from about 10 to about 16 percent by weight ethoxy diglycol and the contents of the vessel are added to the spinning mixture in the beaker.
f) After the ethoxy diglycol is added, from about 0.01-15 percent by weight of a pH modifier such as citric acid, lactic acid or aliphatic acids having a formula C$_n$H$_{(2n+2)}$COOH, (n=1-6) is added to the spinning mixture. This mixture then is spun for approximately one to two hours. After the spinning is finished the mixture is covered and left to sit over-night.
g) The next day the mixture is mixed with a high shear mixer to a uniform consistency with minimal to no air. Air and moisture may be removed during mixing by applying a vacuum from about 0.01 to about 0.1 torr. The mixture is then brought to ambient pressure by adding dry nitrogen.

Combining the Nitrogen Mustard and the Dimethicone or Cyclomethicone Non-Aqueous Vehicle or Carrier That does not include petrolatum or ethanol of Step 2) supra.

In one embodiment, a pharmaceutically acceptable nitrogen mustard.HCl having an essentially completely uniform consistency may be formed by agitating for 60-90 seconds using a high shear mixer to mix 1) an appropriate amount of Nitrogen Mustard having been be reconstituted with an secondary or tertiary alcohol such as isopropyl alcohol, wherein ethanol has been rigorously excluded from the secondary or tertiary alcohol such as isopropyl alcohol, and 2) the appropriate amount of non-aqueous vehicle or carrier that does not include petrolatum or ethanol from step g), supra, wherein the non-aqueous vehicle or carrier does not include petrolatum or ethanol. For example, in an embodiment, a concentration in mg/ml of the pharmaceutically acceptable Nitrogen Mustard.HCl in the non-aqueous vehicle or carrier that does not include petrolatum or ethanol is advantageously from about 1 mg of Nitrogen Mustard.HCl per 100 ml of non-aqueous vehicle to about 2000 mg of Nitrogen Mustard.HCl per 100 ml of non-aqueous vehicle. In another embodiment, a concentration in mg/ml of the pharmaceutically acceptable Nitrogen Mustard.HCl used in a non-aqueous vehicle or carrier that does not include petrolatum or ethanol is advantageously from about 10 mg of Nitrogen Mustard.HCl per 100 m1 of non-aqueous vehicle or carrier that does not include petrolatum or ethanol to about 40 mg of Nitrogen Mustard.HCl per 100 ml of non-aqueous vehicle or carrier that does not include petrolatum or ethanol. In another embodiment, a concentration in mg/ml of the pharmaceutically acceptable Nitrogen Mustard.HCl used in a non-aqueous vehicle or carrier that does not include petrolatum or ethanol is advantageously from about 15 mg of Nitrogen Mustard.HCl per 100 ml of non-aqueous vehicle or carrier that does not include petrolatum or ethanol to about 30 mg of Nitrogen Mustard.HCl per 100 ml of non-aqueous vehicle or carrier that does not include petrolatum or ethanol. This mixture is then poured into a 50 ml flip top plastic cylinder and shipped to the appropriate patient.

The inventors disclose that lower volume containers having from about 0.01 to about 0.2 ml, from about 0.1 to about 0.5 ml, or from about 0.1 to about 1 ml may advantageously be used to provide from 1 to 10 applications of the pharmaceutically acceptable Nitrogen Mustard.HCl over a shorter period of use than the 50 ml flip top plastic cylinders, so that lower amounts of nucleophiles such as ambient water or other ambient nucleophiles such as methanol or ethanol may be introduced into the lower volume containers than when the flip top plastic cylinder is opened to the ambient environment over a period of 100 to 1000 applications. The inventors anticipate decreased decomposition of the free form nitrogen mustard or its HX salt, structure IX, depicted in Reaction 5, supra, when the pharmaceutically acceptable nitrogen mustard is contained in lower volume containers intended for from about 1 to 10 applications. In theory, the chlorides of the free form of the nitrogen mustard or its HX salt may be displaced by nucleophilic attack, such as by water or ethanol, resulting in substitution of the Cl by an OH. Said decomposition of the free form of the nitrogen mustard or its HX salt may be avoided by isolating the nitrogen mustard from traces of water, ethanol or other nucleophiles in the environment. An apparatus 20, as depicted in FIG. 2, infra, depicts this smaller volume container.

Figure 2:
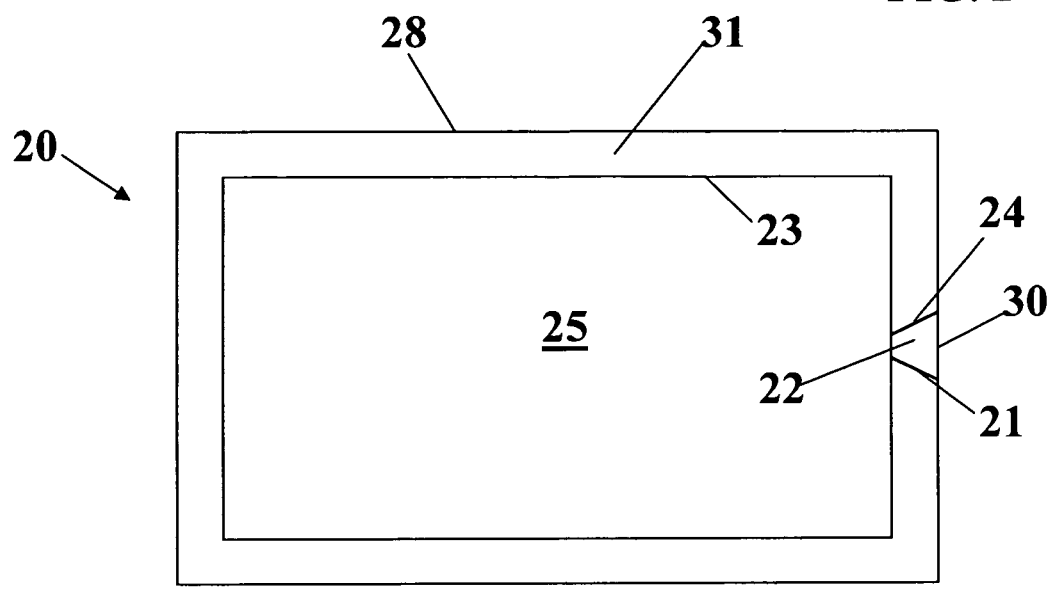
FIGS. 2-4 illustrate a front cross-sectional view of an apparatus having a first compartment, in accordance with embodiments of the present invention.

FIG. 2 depicts a front cross-sectional view of the apparatus 20 for containing the pharmaceutically acceptable Nitrogen Mustard.HCl in the non-aqueous vehicle or carrier that does not include petrolatum or ethanol or the stabilized volatile alkylating agent or HX salt of the stabilized volatile alkylating agent, comprising: a compartment 25 enclosed by a wall 31. The wall 31 comprises an outer surface 28 and an inner surface 23, ends 24 and 21, and opening 30. The first compartment 25 may be charged with the essentially completely uniform mixture of the pharmaceutically acceptable nitrogen mustard.HCl, supra, through the opening 30 . The opening 30 may be closed with plug 22. The plug 22 may be made of the same material as the wall 31, or a lower melting plastic or wax material.

Figure 3:
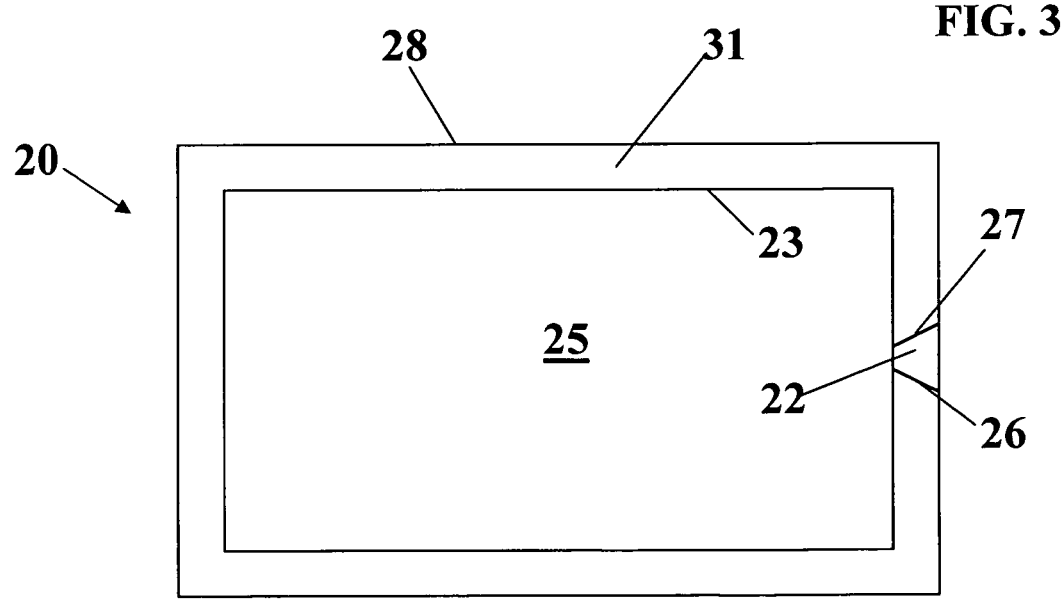
Figure 4:
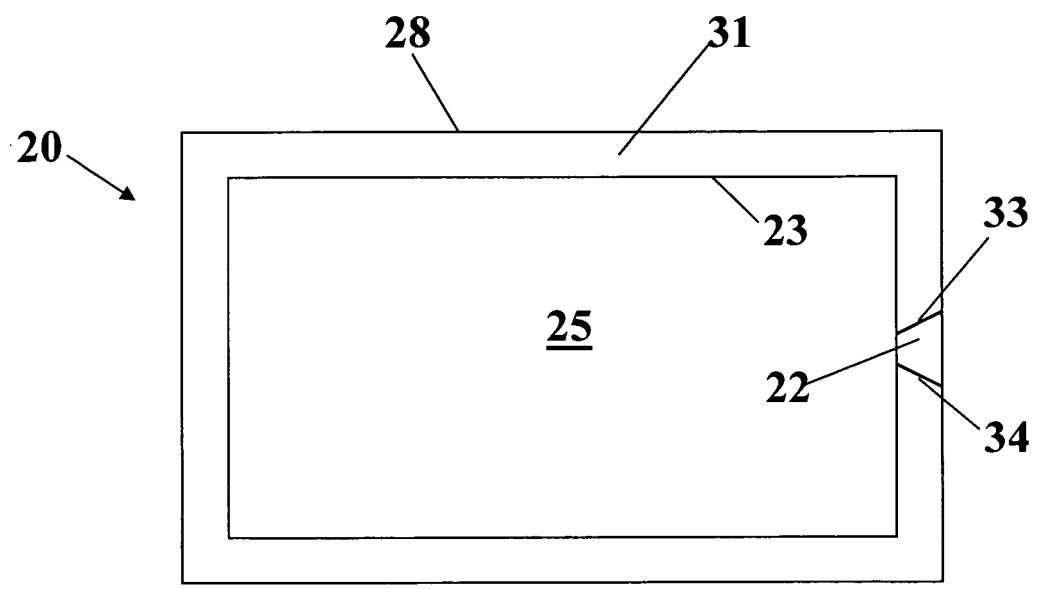

FIG. 3 depicts the apparatus 20, after forming heat seals 26 and 27 by heating the plug 22 and the ends 21 and 24 to their melting points, wherein heating physically and mechanically couples ends 21 and 24 to form mechanically strong heat seals 26 and 27.

FIG. 4 depicts the apparatus 20, after forming serrated perforations 33 and 34 in the plug 22 using a crimping tool or other appropriate device for forming serrated perforations 33 and 34. The serrated perforations 33 and 34 weaken the heat seals 21 and 24 so that they become mechanically less strong, resulting in a tear line for removal of the plug 22 by the patient seeking to apply the pharmaceutically acceptable nitrogen mustard.HCl to a diseased area or area for treatment. In one embodiment, a person wishing to apply the pharmaceutically acceptable nitrogen mustard.HCl to the diseased area or area for treatment may remove plug 22 from the wall 31 of the apparatus 20, restoring the opening 30 in the wall 31 so squeezing or applying pressure to the wall 31 reduces the volume of the apparatus 20, resulting in the pharmaceutically acceptable nitrogen mustard.HCl flowing outward through opening 30 to be applied to the diseased area or area for treatment.

In one embodiment, a concentration of the pharmaceutically acceptable Nitrogen Mustard.HCl in the non-aqueous vehicle or carrier that does not include petrolatum or ethanol in the compartment 25 is from about 1 mg of Nitrogen Mustard.HCl per 100 ml of non-aqueous vehicle to about 2000 mg of Nitrogen Mustard.HCl per 100 ml of non-aqueous vehicle. In another embodiment, a concentration of the pharmaceutically acceptable Nitrogen Mustard.HCl in the non-aqueous vehicle or carrier that does not include petrolatum or ethanol is from about 10 mg of Nitrogen Mustard.HCl per 100 ml of non-aqueous vehicle or carrier that does not include petrolatum or ethanol to about 40 mg of Nitrogen Mustard.HCl per 100 ml of non-aqueous vehicle or carrier that does not include petrolatum or ethanol. In another embodiment, a concentration of the pharmaceutically acceptable Nitrogen Mustard.HCl in the non-aqueous vehicle or carrier that does not include petrolatum or ethanol is advantageously from about 15 mg of Nitrogen Mustard.HCl per 100 ml of non-aqueous vehicle or carrier that does not include petrolatum or ethanol to about 30 mg of Nitrogen Mustard.HCl per 100 ml of non-aqueous vehicle or carrier that does not include petrolatum or ethanol. An orifice or opening 30 may be made by forming an opening in the outer wall 31, through which opening 30 this mixture of the Nitrogen Mustard is then provided by prescription of a physician for treatment of the patient.

The outer wall 31 of apparatus 20 is impermeable to the mixture of step g) or step 9), supra, and/or the reconstituted nitrogen mustard solutions. The wall 31 may be made from elastomeric materials including ethylene/propylene copolymers, ethylene/ethylacrylate copolymers, ethylene/vinyl acetate copolymers, silicone elastomers, medical-grade polydimethylsiloxanes, neoprene rubber, polyisobutylene, chlorinated polyethylene, polyvinyl chloride, vinylchloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylenevinyloxyethanol copolymer; silicone copolymers, polysiloxane-polycarbonate copolymers, polysiloxane-polyethyleneoxide copolymers, polysiloxane-polymethacrylate copolymers, polysiloxane-polymethacrylate copolymers, polysiloxane-alkylene copolymers polysiloxane-ethylene copolymers, polysiloxane-alkylenesilane copolymers, polysiloxaneethylenesilane copolymers, cellulose polymers, methyl cellulose, ethyl cellulose, hydroxypropyl methyl cellulose, cellulose esters, polycarbonates, polyesters, polytetrafluoroethylene, starches, gelatins, natural gums, synthetic gums, and combinations thereof.

Clean-up

All vessels used in the process are placed in a 5% w/v sodium bicarbonate-sodium thiosulfate aqueous bath. Contents are left in the bath for 2 hours and then the washed. The bath is then discarded by normal means. Note: Sodium Thiosulfate reacts with nitrogen mustard to create an innocuous, safe mixture that can be discarded by normal means.

Batches of dispersions of nitrogen mustard were compounded by a pharmacist and included the following components listed in Table 4 (below):

TABLE 4

Nitrogen Mustard Dispersion

| Material Name | Manufacturer/Supplier |
|---|---|
| Hydroxypropyl Cellulose, MXF | Hercules Incorporated (Wilmington, DE) |
| Edetate Disodium Dihydrate, USP | Spectrum Chemicals (New Brunswick, NJ) |
| Menthol, USP | Spectrum Chemicals |
| Butylated Hydroxytoluene, USP | Spectrum Chemicals |
| 2-(2-ethoxyethoxy) ethanol (pharmaceutical grade) | Gattefossé (SAINT PRIEST, Cedex, France) |
| Absolute alcohol, USP | Spectrum Chemicals |
| Propylene Glycol, USP | Spectrum Chemicals |
| Glycerin, USP | Spectrum Chemicals |
| Citric Acid, USP | Spectrum Chemicals |
| Nitrogen Mustard + Sodium Chloride (from the use of Mustargen ®) | Merck & Co. (Whitehouse Station, NJ) |

A second formula comprised:

TABLE 5

Nitrogen Mustard Dispersion.

| Component | Quality Standard | Function |
|---|---|---|
| Mechlorethamine Hydrochloride | USP | Active Pharmaceutical Ingredient |
| Hydroxypropyl Cellulose | NF | Thickening Agent |
| Edetate Disodium, (Dihydrate) | USP | Chelating Agent |
| (DL) Menthol | USP | Cooling Agent |
| Butylated Hydroxytoluene | NF | Preservative |
| Diethylene Glycol Monoethyl Ether (2-(2-ethoxyethoxy) ethanol) | NF | Diluent |
| Isopropyl Alcohol | USP | Wetting Agent |
| Propylene Glycol | USP | Solubilizer |
| Glycerin | USP | Surfactant |
| Lactic Acid (Racemic) | USP | pH Adjuster |
| Sodium Chloride | USP | Ion Releasing Agent |

Stability of Nitrogen Mustard (NM) Ointment Batches

Initial R&D batches of the NM ointment were produced to assess the differences in alcohols used for diluting the NM. Samples were tested at various temperature conditions (5, 25 and 40° C.) and assessed for stability with use of an HPLC assay.

Pilot batch 09-08-05 (~15% ethanol) yielded the following results when tested for stability at 1, 2 and 3 weeks post production (See Table #6).

TABLE 6

Label strength of pilot batch 09-08-05 over time stored at various temperatures.

| Day of assessment | Storage Temperature Label | Strength (%) |
|---|---|---|
| 7 | 5° C. | 96.36 |
|  | 25° C. | 81.37 |

TABLE 6-continued

Label strength of pilot batch 09-08-05 over time stored at various temperatures.

| Day of assessment | Storage Temperature Label | Strength (%) |
|---|---|---|
|  | 40° C. | 20.50 |
| 14 | 5° C. | 92.94 |
|  | 25° C. | 68.44 |
|  | 40° C. | 1.26 |
| 21 | 5° C. | 92.83 |
|  | 25° C. | 58.85 |
|  | 40° C. | −2.22 |

Pilot batch 10-05-05 (~15% isopropanol) yielded the following results when tested for stability at 10, 15 and 20 days post production (Table #7).

TABLE 7

Label strength of pilot batch 10-05-05 over time stored at various temperatures.

| Day of assessment | Storage Temperature | Label Strength (%) |
|---|---|---|
| 10 | 5° C. | 99.54 |
|  | 25° C. | 98.42 |
|  | 40° C. | 79.25 |
| 15 | 5° C. | 99.11 |
|  | 25° C. | 95.75 |
|  | 40° C. | 72.91 |
| 20 | 5° C. | 96.89 |
|  | 25° C. | 93.07 |
|  | 40° C. | 67.48 |

The inventors report that after 18 months of storage at ambient temperature, i.e., between about 20° and about 25° C., there was +/−20% or less loss of the active Mechlorethamine Hydrochloride based on the formulation in Table 5, supra.

The following data revealed that Ethanol caused significant degradation of the NM, where isopropyl alchohol did not. The formulation was changed to reflect these differences (See Table 5 (above).

pH Effects

Figure 5:
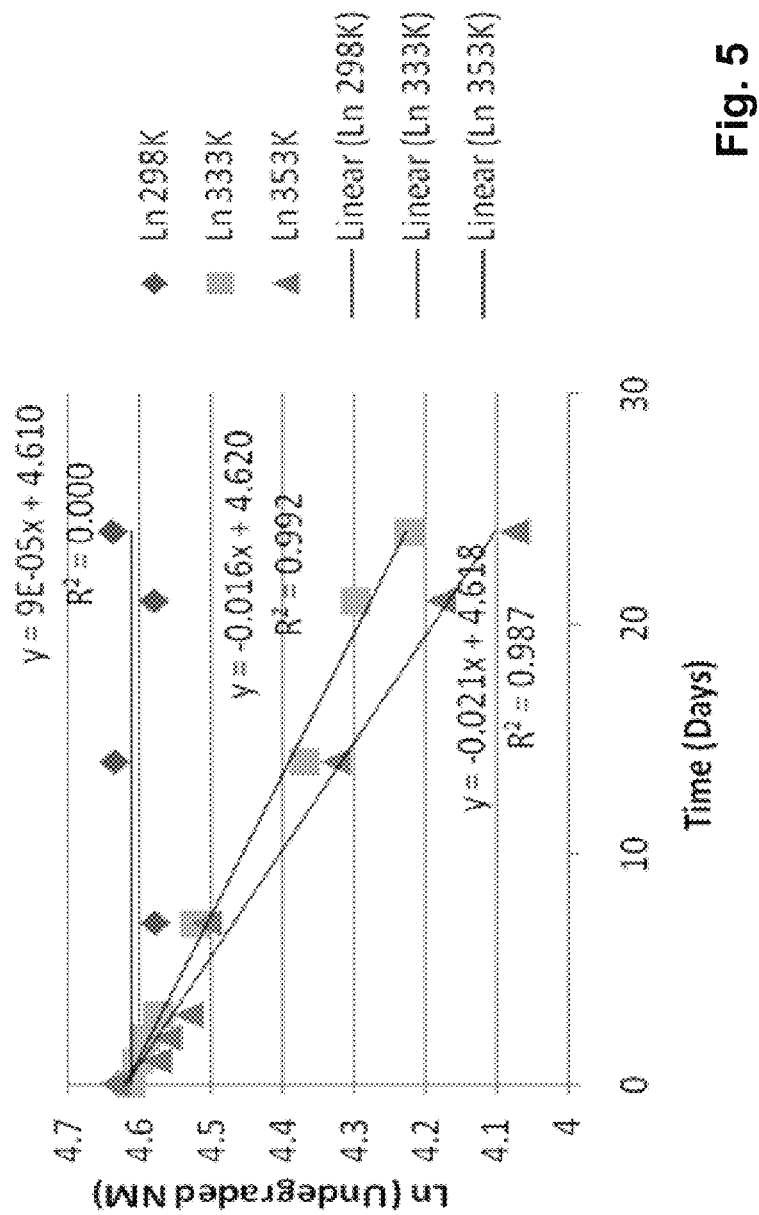
FIG. 5 depicts a Log-linear plot of the stability of MC HCl in 2-(2-ethoxyethoxy) ethanol (2-ethoxy-(2ethoxy) ethanol) at various temperatures over time, in accordance with embodiments of the present invention.

In addition to the above work to optimize the solvent used for solubilizing the NM, work was performed to assess the stabilizing effects of pH on the NM degradation. The following graph, FIG. 5 shows the time course of NM decomposition in different solutions. FIG. 5 shows NM decomposes much faster in pH 7.0buffer, its half-life in this solution is about 2 hours, and FIG. 5 shows NM decomposes totally after 28 hours. FIG. 5 shows NM decomposes faster in higher pH solutions and inorganic salts can accelerate its decomposition too.

In one embodiment, dispersions of pharmaceutically acceptable alkylating agents are dispersed in a pharmaceutically acceptable excipient, e.g., 2-(2-ethoxyethoxy) ethanol (diethylene glycol monoethyl ether) (structure XX, infra) The term "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

The dispersed pharmaceutically acceptable alkylating agents in 2-(2-ethoxyethoxy) ethanol (diethylene glycol monoethyl ether) (structure XX, infra) may be used in the preparation of dispersed systems and other pharmaceutical formulations, and for the storage, transport and dispensing of said dispersions in a stabilized form. Hereinafter, "stabilized" is defined as dispersing the pharmaceutically acceptable alkylating agent in a pharmaceutically acceptable excipient so that the pharmaceutically acceptable alkylating agent undergoes hydrolysis or nucleophilic attack from natural nucleophiles such as water in the environment at a lower rate, compared to the rate that the neat pharmaceutically acceptable alkylating agent undergoes hydrolysis or nucleophilic attack from natural nucleophiles such as water in the environment. Structure XX. Structure of 2-(2-ethoxyethoxy) ethanol.

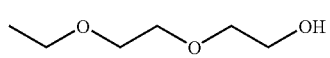

XX

The physical, stability, transport and storage characteristics of the dispersions are significantly different than those of the corresponding pharmaceutically acceptable alkylating agents themselves. These useful characteristics facilitate formulation and production operations and rapid achievement of pharmaceutically acceptable alkylating agent homogeneity in dispersed system products during their manufacture, while simultaneously reducing the potential for airborne and workplace contamination and personnel exposure to the pharmaceutically acceptable alkylating agents.

The pharmaceutically acceptable alkylating agents remain stable in the dispersions across a wide range of temperatures, both in storage and when in use as formulation aids, without requiring the use of antioxidants or other stabilizing agents. These dispersions have utility in imparting desirable physical, stability, transport, storage and dispensing properties otherwise not achievable with the pharmaceutically acceptable alkylating agents themselves.

Such dispersions have a number of uses and applications, such as formulation aids and as concentrated sources of pharmaceutically acceptable alkylating agents for dilution and incorporation into a variety of dispersed systems and pharmaceutical products.

The invention is directed to the preparation of a dispersion of an alkylating agent or agents in 2-(2-ethoxyethoxy) ethanol by forming a dispersion, such as a paste, a coarse dispersion, a suspension, a colloid, a molecular dispersion, or a solution of an alkylating agent using 2-(2-ethoxyethoxy) ethanol as the continuous phase.

Such a dispersion may be prepared by mixing one or more alkylating agents with 2-(2-ethoxyethoxy) ethanol. Said mixing may be accomplished by various means, including flocculation, wetting, levigation, trituration, stirring, blending, homogenizing, sonication, injection, countercurrent exchange, impinging jet mixing, expansion of a supercritical fluid, and milling. Hereinafter, "levigation" is defined as the grinding to a powder of a moist or hard substance, or the mixing of a solid or particulate substance together with a solvating or wetting agent, thereby intimately mixing or coating the solid or particulate with the solvating or wetting agent.

The invention is also directed to the use of such a dispersion as a formulation aid, and as a means of storing, transporting and dispensing discrete quantities of an alkylating agent for use in pharmaceutical formulations and other preparations in the form of a dispersion in 2-(2-ethoxyethoxy) ethanol.

As a formulation aid, such a dispersion serves as a pre-solvated, pre-dispersed form of an alkylating agent for ready dispersion and homogeneous mixing into a pharmaceutical formulation or other preparation, such as a solution, a suspension, an ointment, a cream, a lotion, a plaster, a spray, a colloid and a paste. Such a pre-dispersed form of an alkylating agent, already de-gassed and solvated, facilitates homogeneous mixing into such dosage forms while minimizing or eliminating clumping, flocculation, agglomeration, sticking and caking of alkylating agents.

Such a dispersion might be stored in any suitable container, such as a jar, a bottle, a flask, a bag, a collapsible bag, a bladder, a syringe, a collapsible tube and a drum. Said container might also have an appropriate dispensing port, such as a mouth, a spigot, a valve, a syringe port, and a pump. Said container might also be pressurized, or be charged by or attached to an inert gas source, such as dry nitrogen or helium, in order to further maintain stability of the dispersion and replace the dispensed volume of the dispersion with inert gas.

Mechlorethamine hydrochloride (hereinafter MCHCl) is an alkylating nitrogen mustard employed systemically as a cytotoxic agent for the treatment of cancer and other conditions. MCHCl is also employed topically for the treatment of psoriasis and other dermatological conditions.

MCHCl is an unstable compound, and rapidly degrades to inactive products in the presence of base, water and many pharmaceutical excipients, including alcohols such as ethanol and isopropanol. As such, most MCHCl topical formulations currently employed for the treatment of dermatological conditions are composed of MCHCl dispersed in hydrophobic excipients, such as petrolatum, mineral oil and other lipophilic substances. These products tend to be stiff, have a high skin drag, and leave an adhesive, greasy layer on the skin that may also stain clothing or rub off on others, characteristics not generally acceptable to patients.

Formulation of these products is generally accomplished by mixing MCHCl powder directly into these viscous substances. Thus, the homogeneous incorporation and distribution of the dry powder into the oleaginous vehicle is complicated by clumping, sticking and caking of the dry powder in the vehicle, thereby requiring extensive mixing and homogenizing, as well as levigation and wetting agents not necessarily desirable in the final product. In addition, current formulation methods require repeated handling of the highly poisonous MCHCl powder, which is easily swept up and dispersed in the air, thereby posing a serious contamination risk for both personnel and the manufacturing facility.

Alternative topical formulations employing less lipophilic and amphipathic excipients have been explored. These excipients include 2-(2-ethoxyethoxy) ethanol (FIG. 1), marketed under various trade names, including 2-(2-ethoxyethoxy) ethanol and diethylene glycol monoethyl ether. Although 2-(2-ethoxyethoxy) ethanol has served as an effective vehicle for many drugs, it is a primary alcohol, and many commercial forms of this excipient contain significant amounts of water and other potentially nucleophilic and solvolytic impurities, including the primary alcohols 2-methoxyethanol and 2-ethoxyethanol.

The inventors report, however, that MCHCl may be dispersed in 2-(2-ethoxyethoxy) ethanol across a wide range of concentrations while remaining stable for extended periods of time across a wide temperature range, even though 2-(2ethoxyethoxy) ethanol is a primary alcohol. MCHCl remains stable when dispersed in commercial 2-(2-ethoxyethoxy) ethanol containing 0.1% w/w or more of water, which generally promotes solvolysis of this nitrogen mustard. The inclusion of stabilizing agents, such lactic acid or sodium chloride, has no significant effect on nitrogen mustard stability in the dispersion, and is not necessary for preparing a stable dispersion. Notably, MCHCl remains completely stable when dispersed in 2-(2-ethoxyethoxy) ethanol for over three months at room temperature. Significant degradation of MCHCl in the dispersion is only noted at elevated temperatures. Indeed, less than ten percent of the MCHCl in such a dispersion degraded after storage at temperature as high as 80 degrees Celsius for an entire week.

That MCHCl remains stable in the presence of primary alcohols and water, and without stabilizers, preservatives or cooling, is particularly surprising, as it is known that MCHCl readily undergoes rapid solvolysis and nucleophilic substitution when in contact with many primary alcohols, water and mixtures thereof. This unexpected result, wherein MCHCl, known to be readily degraded in the presence of water and primary alcohols, and at elevated temperatures, remained stable in a 2-(2-ethoxyethoxy) ethanol dispersion for long periods of time at practical working temperatures, is neither obvious nor predictable, and underscores the novelty and utility of such a dispersion and its applications and uses. Indeed, since the pKa of 2-(2-ethoxyethoxy) ethanol and the alkoxy alcohol impurities in 2-(2-ethoxyethoxy) ethanol is lower than that of ethanol, they are theoretically even more nucleophilic than ethanol. Nevertheless, MCHCl, normally labile when exposed to such compounds, is quite stable in this dispersion.

In one embodiment, dispersing an alkylating agent or agents in 2-(2-ethoxyethoxy) ethanol may be a convenient means of storing, handling and dispensing an alkylating agent in the form of said dispersion, and as a formulation aid.

In one embodiment, providing a dispersion, where the type of dispersion so prepared and used is versatile, depending upon its contemplated use, and is selected from the group comprising a paste, a coarse dispersion, a colloidal dispersion, a molecular dispersion, a suspension, and a solution.

In one embodiment, providing a dispersion, wherein the concentration of the alkylating agent or agents dispersed in 2-(2-ethoxyethoxy) ethanol is readily adjustable, depending upon the amount of alkylating agent or agents desired, or the concentration of dispersion desired, and ranges between about 0.01% w/w and about 50% w/w.

In one embodiment, the alkylating agent is selected from the group comprising a nitrogen mustard, a sulfur mustard, Lewisite, an alkyl sulfonate, an ethyleneimine, a nitrosourea, a triazene, an imidazotetrazine, mechlorethamine, chlorambucil, cyclophosphamide, 4-hydroxycyclophosphamide, aldophosphamide, ifosfamide, melphalan, bis-(2-chloroethyl) ethylamine, tris-(2-chloroethyl) ethylamine, carmustine, fotemustine, lomustine, streptozocin, busulfan, dacarbazine, procarbazine, temozolomide, treosulfan, uramustine, hexamethylmelamine, thiotepa, tepa, and pharmaceutically acceptable salts, solvates and polymorphs thereof, and mixtures thereof, and the alkylating agent is provided in a dispersion of an alkylating agent or agents dispersed in 2-(2-ethoxyethoxy) ethanol. "Polymorphism" is defined in materials science is the ability of a solid material such as the pharmaceutically acceptable salts or solvates of MCHCl to exist in more than one form or crystal structure.

In one embodiment, an alkylating agent or agents dispersed in 2-(2-ethoxyethoxy) ethanol is provided for use as a formulation aid, where said formulation aid is employed as a dispersion of a pharmaceutically acceptable alkylating agent or mixture of alkylating agents for subsequent dispersion and dilution into a bulk pharmaceutical product during the formulation and manufacture of said product.

In one embodiment, the dispersion of an alkylating agent or agents serves as a means of storing, transporting and dispensing a dispersion of a pharmaceutically acceptable alkylating agent while maintaining the stability of the pharmaceutically acceptable alkylating agent for a period of time and across a range of temperatures. Said period of time ranges between about 1 day and about 3 years, and said temperature range is between about minus 80 degrees Celsius and about plus 60 degrees Celsius.

The invention will now be discussed by way of certain examples, which illustrate, but in no way limit, the invention.

EXAMPLE 3

Preparation of a representative dispersion.

Mechlorethamine HCl (MCHCl) is readily dispersed in 2-(2-ethoxyethoxy) ethanol by deposing dry MCHCl powder into a suitable container, such as a flask, a vial or a bottle, adding 2-(2-ethoxy ethoxy) ethanol, and dispersing the MCHCl by mixing, such as by stirring, sonicating or shaking.

Accordingly, a 0.5% w/w solution of MCHCl dissolved in 2-(2-ethoxyethoxy) ethanol is readily prepared by placing 25 mg of MCHCl powder in a 25 mL glass vial, adding 4.975 grams of 2-(2-ethoxyethoxy) ethanol, and stirring gently for 1 hour.

Equilibrium solubility experiments revealed that the solubility of MCHCl in 2-(2-ethoxyethoxy) ethanol is approximately 1.6% w/w.

EXAMPLE 4

Stability of mechlorethamine HCL dissolved in 2-(2-ethoxyethoxy) ethanol at various temperatures.

A 0.5% w/w solution of MCHCl dissolved in 2-(2-ethoxyethoxy) ethanol was prepared, and aliquot parts were stored at various temperatures in glass vials sealed from the atmosphere, and tested for stability over time.

The results of these stability studies are presented in Tables 8 and 9, infra.

Table 8 reveals that the inclusion of the stabilizing agents sodium chloride, lactic acid or both do not affect MCHCl stability in 2-(2-ethoxyethoxy) ethanol. Thus, simple dispersions of MCHCl in 2-(2-ethoxyethoxy) ethanol are stable without need of additional excipients and stabilizers, and would serve as useful formulation aids.

Table 9 reveals that, even at elevated temperatures, MCHCl remains stable in 2-(2-ethoxyethoxy) ethanol for significant periods of time, even at temperatures as high as 80 degrees Celsius for 1 week. This further underscores the utility and versatility of the unexpected observation that these simple dispersions of MCHCl in 2-(2-ethoxyethoxy) ethanol are stable and versatile formulation aids while facilitating the storage, transport and dispensing of such alkylating agents in dispersion.

TABLE 8

Stability of mechlorethamine HCl dissolved in neat 2-(2-ethoxyethoxy) ethanol and in 2-(2-ethoxyethoxy) ethanol containing the stabilizing agents sodium chloride, lactic acid or both, stored at room temperature for three weeks.

| Sample Number | Time in Weeks | 0.5% MCHCl in 2-(2-ethoxyethoxy) ethanol | 0.5% MCHCl in 2-(2-ethoxyethoxy) ethanol + NaCl | 0.5% MCHCl in 2-(2-ethoxyethoxy) ethanol + Lactic Acid | 0.5% MCHCl in 2-(2-ethoxyethoxy)ethanol + NaCl + Lactic Acid |
|---|---|---|---|---|---|
| | | Percentage undegraded nitrogen mustard (MCHCl) Remaining in samples stored at ~25° C. (mean ± SD) | | | |
| 1 | Zero  | 102.31 ± 0.71 | 100.43 ± 0.29 | 98.40 ± 1.58  | 102.61 ± 0.53 |
| 2 | One   | 97.31 ± 0.38  | 99.05 ± 0.24  | 103.68 ± 0.14 | 101.11 ± 0.15 |
| 3 | Two   | 102.94 ± 1.21 | 99.39 ± 0.52  | 103.57 ± 0.19 | 104.72 ± 0.07 |
| 4 | Three | 97.43 ± 0.06  | 97.38 ± 0.04  | 95.25 ± 0.11  | 103.96 ± 0.41 |
| 5 | Four  | 103 ± 2.65    | 100.79 ± 0.37 | 100.55 ± 0.10 | 101.33 ± 0.10 |
| 6 | Five  | 99.59 ± 0.05  | 97.23 ± 0.31  | 99.98 ± 0.06  | 104.65 ± 0.27 |
| 7 | Six   | 100.03 ± 0.87 | 97.11 ± 2.56  | 97.08 ± 1.87  | 100.75 ± 5.38 |
| 8 | Seven | 100.15 ± 5.56 | 96.19 ± 2.75  | 96.74 ± 1.58  | 99.07 ± 3.98  |
| 9 | Eight | 98.68 ± 5.04  | 92.18 ± 1.45  | 95.49 ± 3.46  | 96.09 ± 3.65  |

TABLE 9

Stability of MCHCl dispersed in 2-(2-ethoxyethoxy) ethanol at elevated temperatures over time.

| Sample Number | | MCHCl in 2-(2-ethoxyethoxy) ethanol at 60° C. (Percentage ± SD) | MCHCl in 2-(2-ethoxyethoxy) ethanol at 80° C. (Percentage ± SD) |
|---|---|---|---|
| | | Percentage undegraded MCHCl Remaining in samples stored at elevated temperature (mean ± SD) | |
| | Time in Days | | |
| 1 | Zero  | 100.76 ± 0.91 | 103.13 ± 0.86 |
| 2 | One   | 99.63 ± 3.66  | 97.20 ± 6.38  |
| 3 | Two   | 98.79 ± 2.03  | 95.85 ± 3.45  |
| 4 | Three | 96.90 ± 4.9   | 92.98 ± 1.32  |
| | Time in Weeks | | |
| 5 | One   | 92.04 ± 4.06 | 90.66 ± 4.80 |
| 6 | Two   | 78.99 ± 0.99 | 75.73 ± 2.96 |
| 7 | Three | 73.44 ± 4.91 | 65.36 ± 5.51 |
| 8 | Four  | 67.99 ± 3.96 | 58.94 ± 4.96 |

Figure 6:
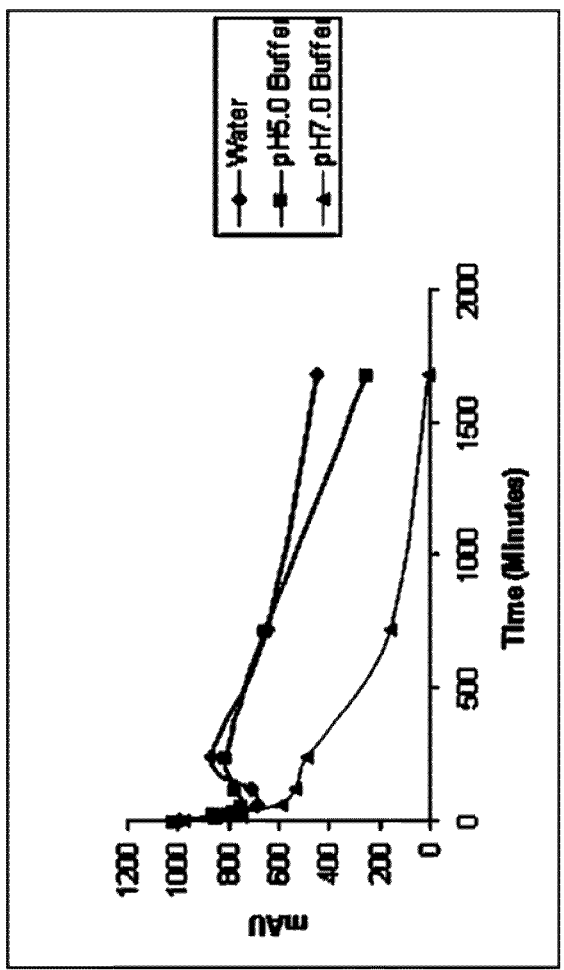
FIG. 6 depicts rate of MCHCl decomposition vs pH, in accordance with embodiments of the present invention.

FIG. 6 depicts a Log-linear plot of the stability of MCHCl in 2-(2-ethoxyethoxy) ethanol 2-(2-ethoxyethoxy) ethanol at various temperatures over time.

In one embodiment, a dispersion, comprising: at least one alkylating agent(s) dispersed in a solvent consisting essentially of 2-(2-ethoxyethoxy) ethanol.

In one embodiment, the dispersion is selected from the group consisting of a paste, a coarse dispersion, a colloidal dispersion, a molecular dispersion, a suspension, and a solution.

In one embodiment, a concentration of the at least one alkylating agent(s) dispersed in the 2-(2-ethoxyethoxy) ethanol ranges from about 0.01% w/w to about 50% w/w.

In one embodiment, the alkylating agent or agents are selected from the group consisting of a nitrogen mustard, a sulfur mustard, Lewisite, an alkyl sulfonate, an ethyleneimine, a nitrosourea, a triazene, an imidazotetrazine, mechlorethamine, chlorambucil, cyclophosphamide, 4-hydroxycyclophosphamide, aldophosphamide, ifosfamide, melphalan, bis-(2-chloroethyl) ethylamine, tris-(2-chloroethyl) ethylamine, carmustine, fotemustine, lomustine, streptozocin, busulfan, dacarbazine, procarbazine, temozolomide, treosulfan, uramustine, hexamethylmelamine, thiotepa, tepa, and pharmaceutically acceptable salts, solvates, polymorphs, thereof, and combinations thereof.

In one embodiment, the dispersion of a pharmaceutically acceptable alkylating agent or agents for subsequent dispersion and dilution is dispersed and diluted into a bulk pharmaceutical product during the formulation and manufacture of the latter.

In one embodiment, the dispersion functions as a means of storing and transporting a dispersion of an at least one pharmaceutically acceptable alkylating agent(s) in liquid form while maintaining the stability of the at least one pharmaceutically acceptable alkylating agent(s) for a period of time and across a range of temperatures.

In one embodiment the period of time the dispersion of the at least one pharmaceutically acceptable alkylating agent(s) in liquid form is stable ranges between about 1 day and about 3 years.

In one embodiment, the temperature range the dispersion of the at least one pharmaceutically acceptable alkylating agent(s) in liquid form is stable ranges between about minus 80 degrees Celsius and about plus 60 degrees Celsius.

In one embodiment, a method of stabilizing at least one alkylating agent(s), comprising:

dispersing the at least one alkylating agent(s) in a solvent consisting essentially of 2-(2-ethoxyethoxy) ethanol.

In one embodiment, a method of formulating a pharmaceutical product, a component of which is an at least one hydrolytically unstable alkylating agent(s), comprising: providing a formulation aid, wherein said formulation aid is a pre-solvated or pre-dispersed form of the alkylating agent; and dispersing the formulation aid into a pharmaceutical formulation or other preparation, wherein the formulation aid and the pharmaceutical formulation are substantially homogeneous.

In one embodiment, a dispersion, comprising: between about 0.001% and about 2.0% by weight of an alkylating agent, or pharmaceutically acceptable salts or solvates thereof; and between about 15% and about 60% by weight of a pharmaceutically acceptable excipient. The pharmaceutically acceptable excipient may be 2-(2-ethoxyethoxy) ethanol. The alkylating agent may be MCHCl.

In one embodiment, a method for treating a person with a skin disorder, comprising: topically applying a dispersion to the affected skin, wherein the dispersion comprises between about 0.001% and about 2.0% by weight of an alkylating agent, or pharmaceutically acceptable salts or solvates thereof; and between about 15% and about 60% by weight of a pharmaceutically acceptable excipient. The pharmaceutically acceptable excipient may be 2-(2-ethoxyethoxy) ethanol. The alkylating agent may be MCHCl.

In one embodiment, a method for stabilizing a volatile alkylating agent, comprising:

dispersing between about 0.001% and about 2.0% by weight of an alkylating agent, or pharmaceutically acceptable salts or solvates thereof and between about 15% and about 60% by weight of a pharmaceutically acceptable excipient. The pharmaceutically acceptable excipient may be 2-(2-ethoxyethoxy) ethanol. The alkylating agent may be MCHCl.

In one embodiment, a method for stabilizing a nitrogen mustard or pharmaceutically acceptable HX salt of the nitrogen mustard, comprising dispersing the nitrogen mustard or pharmaceutically acceptable HX salt of the nitrogen mustard in between about 0.001% and about 2.0% by weight of an alkylating agent, or pharmaceutically acceptable salts or solvates thereof and between about 15% and about 60% by weight of a pharmaceutically acceptable excipient. The pharmaceutically acceptable excipient may be 2-(2-ethoxyethoxy) ethanol. The alkylating agent may be MCHCl.

In one embodiment, a method of treating vitiligo, comprising administering a dispersion to a person in need thereof, wherein the dispersion comprises between about 0.001% and about 2.0% by weight of an alkylating agent, or pharmaceutically acceptable salts or solvates thereof and between about 15% and about 60% by weight of a pharmaceutically acceptable excipient. The pharmaceutically acceptable excipient may be 2-(2-ethoxyethoxy) ethanol. The alkylating agent may be MCHCl.

In one embodiment, a method of formulating a pharmaceutical product, a component of which is an at least one hydrolytically unstable alkylating agent(s), comprising: providing a formulation aid, wherein said formulation aid is a pre-solvated or pre-dispersed form of the alkylating agent; and dispersing the formulation aid into a pharmaceutical formulation or other preparation, wherein the formulation aid and the pharmaceutical formulation are substantially homogeneous.

In one embodiment, is provided a composition for treating a skin disorder, comprising: a Nitrogen Mustard or an HX salt of the Nitrogen Mustard, wherein the Nitrogen Mustard or the HX salt of the Nitrogen Mustard is in a non-aqueous vehicle or carrier, wherein the non-aqueous vehicle or carrier comprises between about 15% and about 60% by weight of a pharmaceutically acceptable excipient, wherein the Nitrogen Mustard is represented by the following structures:

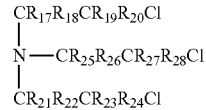

VII

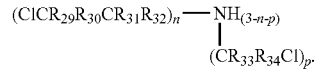

VIII

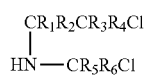

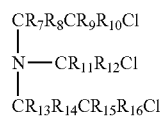

IX

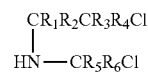

X

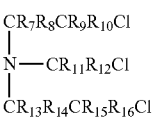

wherein each $R_1, R_2, R_3 \ldots R_{34}$ ($R_1$-$R_{34}$) is independently selected from the group consisting of H, linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, aryl groups, aralkyl groups, alkaryl groups, cycloalkyl groups, bicycloalkyl groups, alkenyl groups, alkalkenyl groups, and alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups alkylenylacyl groups and alkynylacyl groups, wherein n is 1, 2, . . . 3, wherein p is 0, 1, . . . 2, wherein n+p≦3, and wherein any two $R_1$-$R_{34}$ in the same molecule may be linked to form a three- to eight-membered cyclic group. The pharmaceutically acceptable excipient may be 2-(2-ethoxyethoxy) ethanol. The alkylating agent may be MCHCl.

In one embodiment, is provided a method for treating a skin disorder, comprising: administering to a person in need thereof a composition, comprising: a Nitrogen Mustard or an HX salt of the Nitrogen Mustard, wherein the Nitrogen Mustard or the HX salt of the Nitrogen Mustard is in a non-aqueous vehicle or carrier, wherein the non-aqueous vehicle or carrier comprises between about 15% and about 60% by weight of a pharmaceutically acceptable excipient, wherein the Nitrogen Mustard is represented by the following structures:

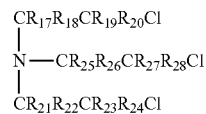

VII

VIII

IX

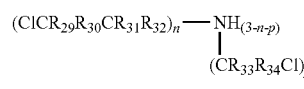

X wherein each $R_1, R_2, R_3 \ldots R_{34}$ ($R_1$-$R_{34}$) is independently selected from the group consisting of H, linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, and a fluorinated cycloalkyl group having 3-17 carbon atoms, aryl groups, aralkyl groups, alkaryl groups, cycloalkyl groups, bicycloalkyl groups, alkenyl groups, alkalkenyl groups, and alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups alkylenylacyl groups and alkynylacyl groups, wherein n is 1, 2, . . . 3, wherein p is 0, 1, . . . 2, wherein n+p≦3, and wherein any two $R_1$-$R_{34}$ in the same molecule may be linked to form a three- to eight-membered cyclic group. The pharmaceutically acceptable excipient may be 2-(2-ethoxyethoxy) ethanol. The alkylating agent may be MCHCl.

The foregoing description of the embodiments of this invention has been presented for purposes of illustration and description. It is not intended to be exhaustive or to limit the invention to the precise form disclosed, and obviously, many modifications and variations are possible.

We claim:

1. A composition for treating a skin disorder, comprising:
a Nitrogen Mustard or an HX salt of the Nitrogen Mustard, wherein the Nitrogen Mustard or the HX salt of the Nitrogen Mustard is in a non-aqueous vehicle or carrier, wherein the non-aqueous vehicle or carrier comprises between about 15% and about 60% by weight of a pharmaceutically acceptable excipient, wherein the Nitrogen Mustard is represented by the following structures:

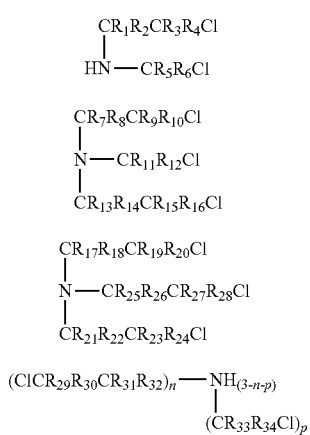

wherein each $R_1$, $R_2$, $R_3$ . . . $R_{34}$ ($R_1$-$R_{34}$) is independently selected from the group consisting of H, a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, aryl groups, aralkyl groups, alkaryl groups, cycloalkyl groups, bicycloalkyl groups, alkenyl groups, alkalkenyl groups, alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups, alkylenylacyl groups and alkynylacyl groups, wherein n is 1-3, wherein p is 0-2, wherein n +P<3, wherein any two $R_1$-$R_{34}$ in the same molecule may be linked to form a three-to eight-membered cyclic group, wherein the pharmaceutically acceptable excipient is 2-(2-ethoxyethoxy) ethanol, and wherein when the composition is applied topically to the skin, there is no clinically significant systemic absorption of the topically applied Nitrogen Mustard.

2. The composition of claim 1, wherein an ingredient of the non-aqueous vehicle or carrier is selected from the group consisting of, Hydroxypropylcellulose, buffer gel, Menthol Crystals USP5, Butylated Hydroxytoluene NF, Glycerin USP, Edetate Disodium USP, Decyl Methyl Sulfoxide, Kris-Ester 236, polyethylene glycol (PEG), ethylene glycol (EG), polypropylene glycol (PPG), propylene glycol (PG), diethylene glycol monosubstituted ether (DGMSE), $HOCH_2CH_2OCH_2CH_2OR_{79}$, wherein $R_{79}$ is selected from the group consisting of a linear alkyl group having 1-6 carbon atoms, a branched alkyl group having 2-12 carbon atoms, a cycloalkyl group having 3-17 carbon atoms, a fluorinated linear alkyl group having 2-12 carbon atoms, a fluorinated branched alkyl group having 2-12 carbon atoms, a fluorinated cycloalkyl group having 3-17 carbon atoms, an aryl group, an aralkyl group, an alkaryl group, a cycloalkyl group, a bicycloalkyl group, an alkenyl group, an alkalkenyl group, an alkenylalkyl group, an alkynyl group, an alkalkynyl group, an alkynylalkyl group, a trifluoropropyl group, a cyanopropyl group, an acryloyl group, an arylacryloyl group, an acryloylaryl group, an alkylacyl group, an arylacyl group, an alkylenylacyl group, an alkynylacyl group, and combinations thereof.

3. The composition of claim 1, wherein the non-aqueous vehicle or carrier comprises propylene glycol USP.

4. The composition of claim 1, further comprising:
Hydroxypropylcellulose, Menthol Crystals USP, Butylated Hydroxytoluene NF, Glycerin USP, Edetate Disodium USP, Decyl Methyl Sulfoxide, or Kris-Ester 236, or any combination thereof.

5. The composition of claim 1, comprising the HX salt of the Nitrogen Mustard, wherein the HX salt of the Nitrogen Mustard is Nitrogen Mustard.HCl, Nitrogen Mustard.HNO₃, Nitrogen Mustard.H₂SO₄, Nitrogen Mustard.HBr, Nitrogen Mustard.HI, or any combination thereof.

6. The composition of claim 1, comprising from about 0.0001 to about 2.0 percent by weight of the Nitrogen Mustard or its HX salt.

7. The composition of claim 1, comprising from about 0.015 to about 0.030 percent by weight of the Nitrogen Mustard of its HX salt.

8. The composition of claim 1, comprising from about 0.01 to about 0.04 percent by weight of the Nitrogen Mustard or its HX salt.

9. The composition of claim 1, comprising the Nitrogen Mustard.

10. The composition of claim 1, comprising the HX salt of the Nitrogen Mustard.

11. The composition of claim 1, wherein the clause: when the composition is applied topically to the skin, there is no clinically significant systemic absorption of the topically applied Nitrogen Mustard; means there is 0% systemic toxicities.

* * * * *

UNITED STATES PATENT AND TRADEMARK OFFICE
CERTIFICATE OF CORRECTION

| | | |
|---|---|---|
| PATENT NO. | : 8,501,817 B2 | Page 1 of 1 |
| APPLICATION NO. | : 12/401812 | |
| DATED | : August 6, 2013 | |
| INVENTOR(S) | : Robert Alonso et al. | |

It is certified that error appears in the above-identified patent and that said Letters Patent is hereby corrected as shown below:

In the Claims

COLUMN 40, LINE 1:

In Claim 1, "wherein $n + P < 3$," should be --wherein $n + P \leq 3$,--

Signed and Sealed this
Third Day of December, 2013

Margaret A. Focarino
*Commissioner for Patents of the United States Patent and Trademark Office*